US007030057B2

United States Patent
Matsumoto (10) Patent No.: US 7,030,057 B2
(45) Date of Patent: Apr. 18, 2006

(54) CATALYST FOR ESTERIFICATION AND TRANSESTERIFICATION AND PROCESS FOR PRODUCING ESTER

(75) Inventor: Satoshi Matsumoto, Kanagawa (JP)

(73) Assignee: Japan Science and Technology Agency, Saitama (JP)

( * ) Notice: Subject to any disclaimer, the term of this patent is extended or adjusted under 35 U.S.C. 154(b) by 669 days.

(21) Appl. No.: 10/275,758

(22) PCT Filed: May 15, 2001

(86) PCT No.: PCT/JP01/04057

§ 371 (c)(1),
(2), (4) Date: Nov. 7, 2002

(87) PCT Pub. No.: WO01/87481

PCT Pub. Date: Nov. 22, 2001

(65) Prior Publication Data

US 2005/0176986 A1    Aug. 11, 2005

(30) Foreign Application Priority Data

| May 19, 2000 | (JP) | ............................ 2000-147554 |
| Jun. 6, 2000 | (JP) | ............................ 2000-169264 |
| Apr. 18, 2001 | (JP) | ............................ 2001-119252 |

(51) Int. Cl.
  *B01J 23/00*   (2006.01)
  *C08G 63/82*   (2006.01)
(52) U.S. Cl. ...................................... 502/350; 528/279
(58) Field of Classification Search ............... None
  See application file for complete search history.

(56) References Cited

U.S. PATENT DOCUMENTS 4,661,622 A    4/1987   Matsumoto

FOREIGN PATENT DOCUMENTS

| JP | 62-234044  |   | 10/1987 |
| JP | 7330684 A  |   | 12/1995 |
| JP | 8 157418 A |   | 6/1996  |
| JP | 2000-1072751 |   | 3/2001  |
| JP | 2001-072751 | * | 3/2001  |

* cited by examiner

*Primary Examiner*—Paul A. Zucker
(74) *Attorney, Agent, or Firm*—Gary C Cohn PLLC (57) ABSTRACT

This invention relates to an activated titanium catalyst used in an esterification reaction and/or a transesterification reaction, and a method of manufacturing esters having a low acid value and narrow molecular weight distribution by making effective use of the excellent dehydration esterification reaction properties and transesterification ability of this catalyst.

18 Claims, 1 Drawing Sheet

Fig. 1

CATALYST FOR ESTERIFICATION AND TRANSESTERIFICATION AND PROCESS FOR PRODUCING ESTER

FIELD OF THE INVENTION

This invention relates to a catalyst for esterification reactions and transesterification reactions, and to a method of manufacturing esters using this catalyst. More specifically, this invention relates to a method of manufacturing esters having a low acid value and narrow molecular weight distribution making use of the ability of the dehydration esterification reactivity and esterification potential of an active titanium catalyst.

BACKGROUND OF THE INVENTION

In the past, catalysts such as sulfuric acid or alkoxytitanium have been used for esterification reactions and transesterification reactions.

However, it is difficult to lower the acid value of the end product of the acid catalyst, while the reactivity of the alkoxytitanium is slow.

To improve the reactivity therefore, and easily remove catalyst residues, attempts have been made to further improve this alkoxytitanium catalyst, such as the polyol polytitanate produced by the reaction of an alkoxytitanium and a low molecular weight polyol (Japanese Patent No. 1795216) or the polytitanic acid arising from reaction of alkoxytitanium and water (Japanese Patent No. 1885399).

When this alkoxytitanium is reacted with a water-soluble polyfunctional polyol, a polyol polytitanate is generated, and if this is further reacted with water, polytitanic acid is generated. When the polyol polytitanate or polytitanic acid are used as catalysts, the polytitanate/polytitanic acid reacts with alcohol and water which produces OH groups on the surface and activates them. However, although the OH groups on the surface are activated, they are consumed as the reaction proceeds, the active sites disappear, and the catalyst becomes inactive.

Dioctyl phthalate has been used as a plasticizer for polyvinyl chloride and it has a very high performance, but in outdoor applications, it volatilizes due to its vapour pressure. In this regard, polyesters or complex esters produced from a dibasic acid, diol and monofunctional alcohol can be used as non-volatile plasticizers. They exhibit excellent properties, and are expected to have the same plasticizer capability corresponding to their viscosity.

If is attempted to manufacture this type of ester using a catalyst of the prior art, the acid value does not decrease if there is not much alcohol present in the system. However, if the alcohol is increased in order to accelerate esterification and reduce the acid value, the polymerization degree does not increase. As the reaction is performed using an amount close to the stoichiometric amount to increase the polymerization degree and produce the polyester, the acid value does not decrease and the specification is still one order of magnitude too high even for electrical components which require a low electrical conductivity. Thus, a low acid value polyester was desired. On the other hand, complex esters having a low polymerization degree and a specific molecular weight, have a molecular weight distribution which decreases exponentially as the number n decreases and have a large number of low molecular weight molecules. This leads to a mixture with a large amount of diester with no diol component, and its separation is very difficult. Due to the heat history during separation, it was extremely difficult to improve the shortcoming that the acid value of the component which it is desired to use in the cycle increases.

Thus, a polyester or complex ester which could be used as a plasticizer for polyvinyl chloride could not be manufactured in an actual production process, and the environmental problem that large amounts of plasticizer continue to be released from polyvinyl chloride has still not been resolved.

PROBLEMS TO BE SOLVED BY THE INVENTION

It is therefore an object of this invention to provide a catalyst which can be used in esterification reactions and transesterification reactions. This catalyst overcomes the aforesaid disadvantages of prior art catalysts based on alkoxytitanium which are used for esterification reactions and transesterification reactions, remarkably accelerates reactivity, suppresses the loss of catalytic activity as the reaction proceeds to the absolute minimum, and since the reaction is a first order reaction, makes it possible to obtain an ester end product having acid value of zero. To lower the acid value, an excess of alcohol could be used, but OH groups remained at the ends of the product, and in prior art acidic and basic catalysts, the alcoholic groups produced, remained. Esters having a large number of terminal OH groups cannot be used for electrical applications, as described above. An acid catalyst identical to that of the prior art was therefore desired having excellent catalytic activity for dehydration esterification reactions, which, although identical to the acid catalysts of the prior art, did not lose its unique activity in transesterification reactions, and which did not lose its catalytic activity even if a transesterification reaction was performed after esterification.

It is a further object of this invention to provide a method of manufacturing esters which permits elongation of reaction products containing ester bonds and OH groups at the ends by transesterification reactions, and which permits manufacture of esters having a desired polymerization degree with a very narrow molecular weight distribution.

Means to Solve the Problem

The first object of this invention is to provide a catalyst for an esterification reaction and/or a transesterification reaction, which is a gel-like substance comprising a mixture of an alkoxytitanium, water-soluble polyol and water, or the reaction product thereof, wherein the number of moles of said water-soluble polyol and said water relative to 1 mole of titanium, is respectively 1–50 moles and 1–60 moles. This alkoxytitanium is preferably tetrabutoxytitanium, tetraisopropyloxytitanium or tetraoctyloxytitanium, and the water-soluble polyol is preferably ethylene glycol, propane diol, diethylene glycol or glycerine.

The second object of this invention is to provide a method of producing an ester comprising, a first step wherein a monofunctional alcohol and diol are simultaneously or separately added to a dibasic acid, a second step wherein the reaction product of said acid and alcohol produced in the first step is separated to obtain an ester, and a third step wherein the reaction product separated in the second step is recycled to the first step, 0.01–10 millimoles, preferably 0.05–5 millimoles and more preferably 0.1–5 millimoles of the catalyst relative to one mole of acid being used in said first step.

The third object of this invention is to provide a method of producing an ester comprising, a first step wherein a diol is reacted with an ester produced beforehand from a dibasic acid and a monofunctional alcohol, or an ester produced beforehand from a monofunctional alcohol and diol, a second step wherein unreacted ester is separated from the product produced in the first step to obtain another ester, and a third step wherein unreacted ester separated in the second step is recycled to the first step, 0.05–5 millimoles of the catalyst relative to one mole of acid being used in said first step.

The term "ester" as used in the context of the present invention is a concept including both polyesters and complex esters, as described hereafter. Also, the term "reaction" refers specifically to only one of esterification reactions and transesterification reactions, or to both esterification reactions and esterification reactions. This is because the catalyst of the present invention is effective for both esterification reactions and esterification reactions.

This is related to the type of dependent transesterification reaction, i.e., to the method of manufacturing complex esters and polyesters by performing a transesterification reaction between a diol and/or its reaction product using the catalytic function of an ester manufactured using an activated catalyst. The dibasic acid may be adipic acid, phthalic acid or a mixture thereof. The number of carbon atoms in the monofunctional alcohol may be 4–10, and the diol may be at least one type selected from among 1,2-propane diol, 1,3-butane diol, 1,4-butane diol, 1,6-hexane diol or 2-ethyl-1,3-hexane diol, polyethylene glycol having a molecular weight of less than 1000, preferably less than 500 and more preferably less than 300, and polypropylene glycol having a molecular weight of less than 1000, preferably less than 500 and more preferably less than 300.

According to this invention, by premixing a polyol and/or water with polyol polytitanate/polytitanic acid, or by adding and simultaneously reacting (esterification reaction or a transesterification reaction) a polyol and/or water to form a reaction system, it is proposed to increase the number of active sites in the polyol polytitanate/polytitanic acid catalyst, to prevent deactivation of polyol polytitanate due to esterification including active sites in the esterification or transesterification reaction, thus extending the lifetime of the active sites, and to remarkably increase the activity of the activated titanium catalyst. When this catalyst is used in a dehydration esterification, the reaction proceeds as a first order reaction in direct proportion to the logarithm of the acid concentration.

This polyol water active titanium is produced by dissolving and reacting an alkoxytitanium with a polyol and water in the proportion of 1–50 moles polyol and 1–60 moles water to one mole of titanium so as to obtain a gel product containing an excess amount of water which is the feature of this polytitanate. This gel is then suspended in a solvent or the alcohol used for the reaction, and added to the reaction system.

Figure 1:
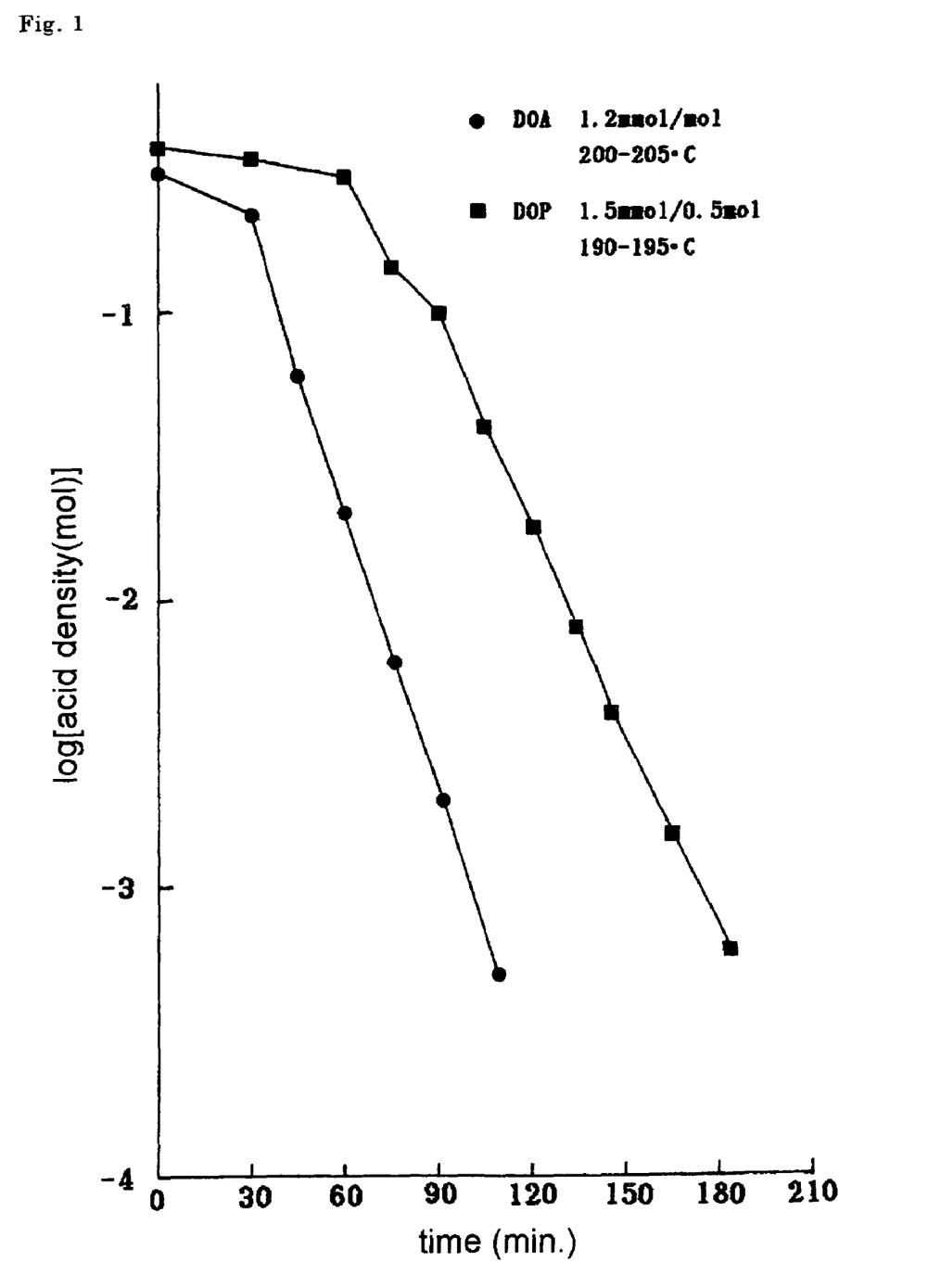
FIG. 1 shows a variation of concentration in the esterification reaction using the active titanium catalyst of this invention.

If this catalyst is used, as shown in FIG. 1, dehydrated esters react in a first order reaction which is much more rapid than the reactions of the prior art. This means that the end point of the reaction can be predicted, and after a certain time has elapsed from the measurement, a reaction product having an effective acid value of zero can be obtained. Using this catalyst, it is possible not only to obtain esters having an acid value lower than that of the acids usually used as catalysts, but the acid value can easily be lowered with ester products having a high acid value or esters whereof the acid value has increased due to deterioration or the like.

According to this invention, the acid value of diester compounds which are used excessively in the following transesterification reaction and recovered, and whereof the acid value has increased due to thermal decomposition, can easily be lowered in a short time so that they can be re-used. In other words, the diesters can be recycled.

The fourth object of this invention is to provide a method of producing an ester comprising a step of reacting a reaction product, comprising an ester composition (RO(COACOOX)$_n$H) (n≧1) formed from the reaction of a dibasic acid (HOOCACOOH), diol (HOXOH) and terminal alcohol (ROH), in the presence of a catalyst according to claim 1 or 2 under a reduced pressure of 100 mm Hg or less. It is preferred that this reactive ester composition is the reactive ester composition (RO(COACOOXOH) wherein the dibasic acid (HOOCACOOH), diol (HOXOH) and terminal alcohol (ROH) are present in the molar ratios 1:1:1.

It is also preferred that this reaction product contains an ester compound represented by the general formula:

$$R'O(COACOOXO)_nCOACOOR'$$

(in the formula, R' are respectively alkyl groups which may be identical or different, and may be identical to the aforesaid R).

This active titanium catalyst has catalytic activity for both esterification reactions and transesterification reactions, and as it has a superior activity for esterification reactions in particular, use can be made of this property to produce and react an ester alcohol and the aforesaid esters in an esterification process, which is the fifth object of this invention.

Specifically, when the dehydration esterification which is the first step of this invention is performed using the active titanium catalyst comprising a dibasic acid, diol and monofunctional alcohol, the required amounts of monofunctional alcohol (R) and diol (X) are distributed and continuously introduced into the reactor so that the production of diester (RAR) is suppressed as far as possible, and the conditions are adjusted so that the complex ester (R(AX)$_n$AR, n≧1) and ester alcohol (RAX) can coexist in the reaction system. In other words, in this esterification reaction, if a high concentration of the alcohol (R) is introduced, the undesirable diester (RAR) is produced. Due to the production of this undesirable diester (RAR), the excess amount (of alcohol) must be suppressed to the degree at which the ester alcohol (RAX) can coexist with the complex ester.

Regarding the addition of alcohol, if the excess amount is reduced, there is the problem of the addition concentration. Hence, when the dibasic acid (A) and diol (X) are reacted, it is preferable to add the alcohol (R) a little at a time, and to reduce the reaction temperature to 150–165° C. In a reaction using adipic acid (A), at this stage, the reaction proceeds at a sufficient rate even without a catalyst. The required amount also depends on the extent of the reaction. In the manufacture of the target product R(AX)$_m$(AX)$_n$AR (m≧0, n≧1), an excess amount of the alcohol (R) is used compared to the stoichiometric amount required to obtain R(AX)$_m$(AX)+R(AX)$_{n-1}$AR to perform the esterification reaction. The amount of the alcohol (R) is excessive relative to the target product, but the stoichiometric amount of the esterified product including the diol is obtained even if the whole amount is reacted, so from this viewpoint it is not excessive. Further, as water is excluded from the reaction system and the reaction takes place under anhydrous conditions, quantitative control of the reaction of the lower diol (X) is not easy. The diol component is removed from the reaction system corresponding to the reaction rate and water distillation rate, so it fluctuates largely depending on reaction molar amounts and it is difficult to perform a stoichiometric reaction, but the reaction amounts of each component must be controlled. If the alcohol reaction amount is insufficient due to the distillation of the diol, the alcohol amount will be insufficient even if the amount of the alcohol (R) is controlled, so the acid value does not decrease, the transesterification reaction of the next step does not take place, and low volatility components in the reaction product including ester alcohols, increase. On the other hand, if the addition rate of the alcohol (R) is too high or an excess amount is used, the production amount of diester (RAR) increases, so that not only does the amount removed increase, but the polymerization degree of the reaction product increases correspondingly and a reaction product having the target polymerization degree cannot be obtained. Due to the use of the highly activated catalyst of this invention, the reaction between very small amounts of acid and alcohol is a first order reaction, and the reaction proceeds rapidly even with minor components. Hence, a quantitative reaction can be performed, and esters ranging from polyesters of high molecular weight to complex esters of low molecular weight having a target polymerization degree with a narrow distribution, can now be manufactured.

Next, a transesterification reaction which is the second step, is performed. Specifically, a complex ester $R(AX)_{n-1}AR$, $n \geq 1$) and ester alcohol ($R(AX)_m AX$) are reacted to produce a desired ester ($R(AX)_m(AX)_n AR$). When m in the ester alcohol ($R(AX)_m AX$) is large, the ester is a polyester, while for a complex ester, it is an alcohol ester (RAX) corresponding to m=0.

Thus, esters having a molecular weight distribution of 2 or less can be manufactured. In this case, the molecular weight distribution refers to Pw/Pn (Pw is weight average polymerization degree, Pn is number average polymerization degree).

As a result of the method of this invention, an excellent molecular weight distribution is obtained, and in the complex esters ($R(AX)_n AR$, $n \geq 1$) which have a low polymerization degree, terminal alcohol polyesters, and diester (RAR) side products corresponding to n=0, which were the most difficult problem to overcome, are now suppressed.

If the method of this invention is not adopted, the introduction amounts of alcohol (R) and diol (X) in the esterification reaction are not controlled, or a prior art catalyst without strong esterification and transesterification catalytic activity is used, it is difficult to obtain the product in a stable process.

Using the method of the present invention, polymerization of the complex ester produced is suppressed, and the molecular weight distribution is narrow. In addition, the acid value can be reduced, transesterification is easy and a product having a desired molecular weight can be manufactured. The rated values of the polyesters already on the market can thus be considerably improved. In complex esters, high molecular weight compositions decrease, the viscosity of the product falls and diester side products decrease, so superior complex esters can be manufactured. It is expected that these will be useful as plasticizers of low viscosity having superior plasticizing properties, which do not have any marked volatility, and which are environment-friendly.

When an active titanium catalyst is used, its catalytic activity may fall. This is probably due to absorption or reaction with the titanium catalyst depending on the type of polyol component, covering of active sites and suppression of acid absorption leading to decline of catalytic activity. When ethylene glycol is used for catalyst activation, the decline of activity is relatively small, so this catalyst therefore has excellent activity and retained its activity. If another diol component such as propane diol is used in the activated catalyst to avoid introduction of ethylene glycol in an esterification reaction between a diol and an acid, the activity may decline at the end of the reaction even though some diol apparently remains. In a reaction system where the activity had declined due to the diol component, the same reaction rate cannot be obtained even if activation is performed using the same diol component. Even in this case, using ethylene glycol-water, the catalyst may be adjusted by a solvent, alcohol or a diol. However, if an alkoxytitanium is dissolved to prepare a catalyst and this is then added, it exhibits excellent activity and the acid value can then effectively be lowered.

Specifically, the fifth object of this invention is to provide a method of producing an ester comprising a step of a dehydration esterification reaction and a following transesterification reaction of a dibasic acid, diol and monofunctional alcohol using the catalyst. This active titanium catalyst is a gel comprising an alkoxytitanium, water-soluble polyol and water mixture or the reaction product of this mixture, the proportions of water-soluble polyol and water being 1–50 moles and 1–60 moles relative to one mole of titanium. The required amounts of said monofunctional alcohol and said diol are distributed and continuously introduced into a reactor over the whole period of the esterification reaction.

It is preferred that the dehydration esterification reaction is performed under conditions such that a complex ester and ester alcohol are produced and coexist together.

Further, when the target product of the manufacturing method of this invention is represented by $R(AX)_{m+n}AR$ ($m \geq 0$, $n \geq 1$, A is a dibasic acid, X is a diol and R is a monofunctional alcohol, the reactive groups and ester bonds being omitted), the amount of said monofunctional alcohol (R) used in said dehydration esterification reaction is obtained by adding 0.2–2.0 times, particularly 0.5–1.0 times the difference between the amount required to obtain $R(AX)_m AX + R(AX)_{n-1}AR$ as the product of the dehydration esterification reaction and the stoichiometric amount required to obtain $R(AX)_{m+n}AR$, to the stoichiometric amount required to obtain $R(AX)_{m+n}AR$.

In this case, the aforesaid difference R is equal to one mole. $R(AX)_m AX$ may be considered as separate parts $R(AX)_m$ and RAX, and the stoichiometric amount in this case is increased by 2R so that 2R is used as the excess amount. The excess amount is determined by the ratio m/n of the polymerization degrees of the target substances. It may be an amount less than 1 to an amount of several times, but if it is less than 0.33, the molecular weight distribution widens, and it is less than 0.2, its proportion is low and its effect is unclear. If it is too large, RAR increases so there is no effect. It is therefore preferred to use 0.2–2.0 times an amount relative to the difference from the stoichiometric amount, as the excess amount.

By distributing this amount and introducing it continuously into the reactor, the aforesaid dehydration esterification reaction takes place under conditions wherein a complex ester and ester alcohol are produced together.

Further, according to this method, the molecular weight distribution of the ester produced is 2 or less, so a complex ester having a narrow molecular weight distribution can be manufactured.

Herein, the term "esters" is used in the sense of including both polyesters and complex esters which are described in detail hereafter.

DESCRIPTION OF THE PREFERRED EMBODIMENTS

The catalyst of this invention is a mixture of an alkoxytitanium, water-soluble polyol and water, or the reaction product of this mixture.

Herein, alkoxytitanium includes tetrafunctional tetraalkoxytitaniums such as tetrabutoxytitanium and its tetramers, tetraisopropyloxytitanium, tetraethoxytitanium and tetraoctyloxytitanium, alcohol solutions such as titanium trichloride and titanium tetrachloride and compounds known as orthotitanic acid esters, but tetrabutoxytitanium, tetraisopropyloxytitanium or tetraoctyloxytitanium are preferred, and tetrabutoxytitanium is more preferred. There is no particular limitation on the water-soluble polyol provided that it is a water-soluble compound having two or more hydroxyl groups, but ethylene glycol, propane diol, diethylene glycol or glycerine is preferred.

In this invention, the proportion of water-soluble polyol of this alkoxytitanium is preferably 1–50 moles, preferably 5–20 moles and more preferably 8–15 moles, and the proportion of water is 1–60 moles, preferably 4–40 moles and more preferably 10–20 moles relative to one mole of titanium in this alkoxytitanium.

These may simply be mixed together, heated together or dissolved in a solvent, and there is no limitation on the mixing sequence.

The mixture of alkoxytitanium, water-soluble polyol and water reacts at room temperature to form a gel.

It appears that this structure has a spherical form containing water on the inside, and is coated with a polyol polytitanate. It is also thought that a large number of OH groups are present on the outer surface which accounts for the catalytic activity.

As is known from the prior art, when an alkoxytitanium is mixed with a polyol, a polyol polytitanate is produced, whereas, when an alkoxytitanium is mixed with water, it becomes polytitanic acid, and if methanol and water are added to and reacted with it, there are OH groups appeared on the surface which develop catalytic activity. However, the catalyst of this invention not only has a much higher catalytic activity than the polyol polytitanate/polytitanic acid of the prior art (FIG. 1), but practically suffers no catalyst deterioration over time. Hence, catalyst of this invention has an effect which could not be envisaged in the prior art. It is thought that this excellent result is due to the unique structure described above.

According to this invention, complex esters and polyesters can be manufactured by esterification reactions, and mainly, transesterification reactions, using the titanium catalyst of this invention. However, it may be used for manufacturing only the esterification reaction products of the first step, in which case product can be obtained simply by adding water and filtering off the titanium. Concerning transesterification reactions, the reaction mole ratio of the diols and esters used is important. The larger the amount of diesters, the more lower viscosity products of a low polymerization degree tend to be obtained, and conversely, the larger the molar ratio of diols, the more products of high polymerization degree tend to be obtained. The reaction molar ratio is determined according to the polymerization degree of the target product, and diol diesters are also used as the diol component.

Due to this structure, an excess of diester, for example 4 moles relative to 1 mole of diol, is used to obtain a low viscosity product. Two moles is an excess, and even if a reaction amount of 2 moles or less is used, the amount of unreacted diester remaining must be recycled. At high temperature, apart from the coloration due to the catalyst, volatile acids such as for example phthalic anhydride are produced by thermal decomposition, so a reduced pressure concentration device which has a sufficiently large heating amount should be provided if possible, and it is more preferred that this should have continuous operation.

In the ester manufacturing method carried out by the Inventor so far, the best way of controlling the molecular weight distribution was to gradually add an octanol, which is a terminal alcohol, and in the transesterification reaction, if the reaction is performed while gradually adding a diol, the proportion of the transesterification reaction due to the octanol can be reduced and a product close to the target product can be obtained. However, the higher the polymerization degree, the less it is possible to avoid the effects of the transesterification reaction due to the octanol. As a result, the molecular weight distribution of the target product contains a high proportion of low polymers but also contains high polymer components (wide molecular weight distribution).

The type of complex ester products obtained in the dehydration esterification reactions and transesterification reactions of complex esters depends to some extent on the type of components. Ethylene glycol and diethylene glycol are additives with a poor water resistance and can be destroyed by microorganisms. Ordinary diols having 3–8 carbon atoms and polypropylene glycol have fairly similar properties, and the diol side chain improves water resistance (Japanese Patent Application Public Disclosure Hei 6-172261).

In general, a straight chain adipic acid is used as the acid, but unsaturated acids or aromatic acids are also used. With phthalic acids, the viscosity rapidly increases as the degree of homopolymerization increases, but if they are partially mixed for use as plasticizers, a product having excellent physical properties such as water resistance and resistance to migration, is obtained. Monohydric alcohols having a terminal group are not limited to the octanol of the embodiment, and other alcohols having four or more carbon atoms may be used. In lower alcohols, water resistance is poor, and the higher the alcohol, the more evident the effect of the long chain is. As an example of another type of alcohol, polyethylene glycol monoalkylethers have been noted to suppress the growth of fungii.

The reaction process will now be described. As mentioned above, dioctyl adipate which is a diester of adipic acid and a diol ester are manufactured separately. Adipic acid is added to the diester to reduce the proportion of retroreaction wherein the target is n=2, but n=1 also occurs as a side product.

In this reaction, the octanol produced in the transesterification reaction reacts again, and if the reaction proceeds still further, it may lead to removal of the diol.

Thus, the purpose of the addition reaction is to reduce the proportion of retroreaction. Polyesters of any desired polymerization degree can be obtained by adjusting the molar ratio of diol diester and diester, which is useful for example to obtain polyesters of high polymerization degree.

HOCOACOOH+2HOXOH→HO(XOCOACOO)XOH
HO(XOCOACOO)XOH+nROCOACOOR→
ROCOACOOXO)nCOACOOR+ROCOACOOR

These can be added to the reaction system separately, which is useful to obtain a hetero complex ester, but the diol diester may also added in admixture. With a hetero complex ester, a hetero dibasic acid diester is produced as a side product in the retroreaction and must be separated, so it is advantageous to add the diester and perform the transesterification reaction while removing octanol under reduced pressure. A different diol diester may be added alone or in admixture, the molar ratio of the diol diester and diester determined, and the diol diester added to the diester to carry out the transesterification reaction and obtain the product.

nHOCOACOOH+C$_6$H$_4$(CO)$_2$O+2n+1 HOXOH→
nHO(XOCOACOO)Nxoh+HO(XOCOC$_6$H$_4$COO)
  nXOH→+2n(n+1)ROCOACOOR→
RO(COACOOXO)$_n$(COC$_6$H$_4$COOXO)$_m$COACOOR+
  ROCOACOOR In this addition reaction, even if it is attempted to perform the addition rapidly and remove alcohol, if the octanol produced is not removed from the system within sufficient time, the aforesaid diol removal reaction occurs or different acid diesters are produced, so the molecular weight does not increase. On the other hand, when a homo complex ester is manufactured, a transesterification reaction may be performed while heating the mixture, and the reaction carried out while adding the diol and diol diester. In another method, a mixture of an ester alcohol and a diester is prepared by a dehydration esterification, and a transesterification reaction is then performed (Japanese Patent No. 2517245). In this case also, products having different polymerization degrees can be obtained by varying the molar ratio of ester alcohol and diester.

2n+1ROH+n+1HOCOACOOH+HOXOH→
ROCOACOOXOH+nROCOACOOR→
RO(COACOOXO)$_n$COACOOR+ROCOACOOR

In this reaction, an addition esterification reaction can subsequently be performed to obtain the target product.

Specifically, a mixture of the ester alcohol and diester is prepared (Step A), the diester to be recycled is added (Step B), the temperature is temporarily lowered to about 140° C. and the reaction molar ratio is adjusted, and the transesterification reaction (Step C) is then started by increasing the degree of pressure reduction while gradually raising the temperature. By maintaining conditions of 200° C., 25 mm Hg, the transesterification reaction takes place and after removing sufficient alcohol, the addition esterification reaction of the next step (Step D) is performed. The feature of this two-step transesterification reaction is as follows. In the esterification reaction (A) for manufacturing the ester alcohol and ester, corresponding to the reaction molar ratio, the diol component represents an excess of alcohol, and when the diester is manufactured, about 20% excess alcohol is used. Consequently, a step is required to remove the excess alcohol prior to the transesterification reaction. However, the esterification reaction (C) can be performed without any excess alcohol at all.

In the following addition esterification reaction (D), when manufacturing a hetero complex ester, if a retroreaction occurs and diol is removed, even if the diol participates in further reactions, dioctyl phthalate which is a side product mixes with recycled diester, so a step is required to separate and remove it. In practice, in a batch reaction, diester which is produced as a side product cannot be re-used, so the cost increases due to the side product diester, and the manufacturing process is not profitable. If the complex ester is required to have water resistance, the diol and hetero complex ester are expensive, and in the case of a hetero complex ester, re-use of the side product diester was a problem. In this addition transesterification reaction, the reaction is performed by the diol diester of phthalic acid. A reaction due to dioctyl phthalate occurs due to transesterification in the mixed liquor. This is a transesterification, or an ordinary dehydration esterification reaction followed by a transesterification reaction to reduce the volatile component, wherein a step (E), further simplifying the structural formula and abbreviating the different acids as A, P, alcohol as O and diol as X, occurs with a considerably high probability in the presence of a titanium catalyst. This reaction can be prevented by an addition transesterification reaction, so the side product diester can be recycled and re-used.

3ROH+HOCOACOOH+HOXOH→(A)
ROCOACOOXOH+ROCOACOOR→+ROCOACOOR
  (B)→
RO(COACOOXO)nCOACOOR+ROCOACOOR(C)→+
  HO(XOCOC$_6$H$_4$COO)XOH→(D)
RO(COACOOXO)$_n$(COC$_6$H$_4$COOXO)$_m$COACOOR+
  ROCOACOOR
OAO+HOXPXOH+2OAO+O→OAXPO+HOXAO+
  OAO→OAXOH+OPO+OAXAO→OPO+OAXAXAO
  (E)

Regarding the product of a sequential addition esterification reaction, if an excess of octanol is used in the transesterification reaction, an ester alcohol is produced so it is necessary to perform a transesterification at the end of the reaction, and this process can be used.

It is a feature of the catalyst that the reaction rate is greatly enhanced, and the reaction proceeds as a first order reaction. This means that a reaction takes place even between very small amounts of acid and alcohol, and that a reaction takes place with only a small excess provided that it is a stoichiometric excess. During the esterification of a dibasic acid, diol and terminal alcohol, considering the intermediate products of an ester alcohol and a diester, an excess of ROH is theoretically necessary, and if the esterification reaction can proceed sufficiently with this excess alone, the excess can be removed by a transesterification reaction.

Experimental results show that due to the use of the catalyst of the present invention, the reaction proceeds at a sufficient reaction rate with the stoichiometric excess, and target composition esters with a low acid value and excellent molecular weight distribution can be manufactured. It is thus possible to prevent the excess alcohol which is generally used from acting on the product, leading to a transesterification reaction, and polymerization (isomerization) to diesters and esters of high polymerization degree, and as a result, esters having a superior composition can be manufactured.

ROH+HOCOACOOH+HOXOH+ROH+HOCOACOOH+
  HOR→
ROCOACOOXOH+
  ROCOOACOOR→ROCOACOOXOCOACOOR+ROH

In complex esters of low polymerization degree and isomeric complex esters, concerning the use of excess diol and terminal alcohol, the purpose of the reaction can be achieved assuming a complex ester having n greater by 1 corresponding to the use of excess diol.

ROH+nHOCOACOOH+nHOXOH+HOCOACOOH+
  2ROH→
RO(COACOOXO)$_n$H+ROCOACOOR
  (n1ROCOACOOXOH+ROCOACOOXOCOACOOR)→
  RO(COACOOXO)$_n$COACOOR+ROH

Due to the use of this excellent catalyst, with polyesters, a stoichiometric composition can be reacted in close to the stoichiometric amount, so a superior composition can be obtained. However, it is effectively impossible to carry out the transesterification reaction quantitatively in the proportion of one diester for one ester alcohol. Thus, polyesterification takes place, and correspondingly, unreacted diester remains so that side products cannot be prevented.

With polyesters, transesterification occurs with the polyester, so side product diesters can be ignored and a product having an excellent distribution can be obtained. With lower complex esters, a manufacturing method is adopted wherein side products are reduced by making the transesterification reaction a reaction with a complex ester. It is needed to treat the diesters which are produced as side products in the reaction as complex esters in the aforesaid two-step transesterification reaction, and use unreacted diester as a starting material for the recycling reaction.

When complex esters are used as plasticizers, excellent properties are obtained by using hetero complex esters. There is no particular need to attain high molecular weights, and superior plasticizer properties are obtained the lower the viscosity is. In the case of low volatility plasticizers used for electrical applications of the prior art, polyethylene is used in conjunction with other resins, so a plasticizer was desired with little migration within the resin or to other resins. For this purpose, the molecular weight is increased, but as it is fairly difficult to control the molecular weight distribution, low molecular weight fractions are removed, designers aim for a higher molecular weight than is necessary, and substances having a molecular weight in the range 2000–4000 are used. It was thus difficult to reduce its viscosity and acid value. Judging from the experimental results obtained by the Inventor so far, not only a straight chain part but with partial use of phthalic acid, a scissors-shaped part, is formed in the molecule, and it is disclosed in Japanese Patent Application Public Disclosure Hei 8-157418 that as a result, there are few migrations not only within vinyl chloride (transitions from a high density to a low density plasticizer), but also to polyethylene. In addition, regarding plasticizer applications, low molecular weight adipates are hydrolyzed when used under high humidity and their surface whitens, so water resistance was required. With this objective, properties can be improved by incorporating 0.3 or more units of phthalic acid. As a plasticizer for polyvinyl chloride, dioctyl phthalate has been used and it has excellent properties, but in outdoor applications, it evaporates due to its vapour pressure. In this regard, complex esters have excellent properties as non-volatile plasticizers, and exhibit identical plasticizer properties corresponding to the viscosity of the plasticizer. The usage proportion of plasticizer, having an identical hardness to that of 50 parts of DOP, is 52 parts or less for a complex ester having a viscosity of 500 centipoise and polymerization degree of up to 5, and this number drops to 46 for a polymerization degree of 1. As the adipic acid content increases, low temperature properties increase and there are also cold resistance applications, however the increase in polymerization degree is adversely affected. Low molecular weight complex esters exhibit a higher plasticity, but it is difficult to manufacture them only with n=1, so they are manufactured selectively for plasticizer applications according to the ease of manufacture and a manufacturing cost corresponding to the desired properties.

Complex esters have the general formula: ROCOA-COOXOCOACOOR (in the formula, R is an alkyl group of a terminal alcohol, A is mainly an acid residue of adipic acid ($-CH_2CH_2CH_2CH_2-$), and X is an alcohol residue of the diol used (e.g., $-CH_2CH(CH_3)-$: propane diol)). They have been used as low temperature lubricating oils, and it is thought that, because the esters of this invention have a low acid value and low OH value, when using a diol component which has low temperature properties and adipic acid, they exhibit excellent characteristics for their intended use. The Inventor discovered that even if it was intended to manufacture complex esters which are generally manufactured as composite esters, mixtures are obtained as represented by the integer n in RO(COACOOXO)$_n$COACOOR. In particular, in the manufacturing method, a composition was obtained comprising plural substances in different proportions, and their proportion decreased as the value of n increased, differentiating it from composite esters. Therefore, the molecular weight shows the average value for the mixed composition, e.g., 1.5 represents an equimolar mixture of n=1 and n=2. From experimental results obtained previously, it has been found that even if it was attempted to produce RO(COACOOXO)COACOOR, if one mole of RO(COACOOXO)$_2$COACOOR was produced as a side product, one mole of ROCOACOOR was produced corresponding to the increase in the value of n. Using this fact, if the number of moles of ROCOACOOR, obtained by subtracting the weight of yield product from the weight of target product, is calculated, and the value of n in the product RO(COACOOXO)$_n$COACOOR is calculated assuming that the number of moles of target product obtained by subtracting this number of moles, is produced, the average molecular weight of the product can be calculated. If the molecular weight of the complex ester is calculated in this way, the reaction can be treated quantitatively. Likewise, the polymerization degree of diol diesters is identical in principle. The value obtained by subtracting the stoichiometric amount shown in ( ) of adipic acid ester from the weight of the reaction product of diol diester represented by HO(XO)COACOO)$_n$XOH and dividing by the molecular weight of HOXOH, represents the number of moles of the product, and assuming that its inverse represents the value of the polymerization degree n, the molecular weight can be calculated. It should be noted that in the examples, empirical formulae are shown. Adipic acid is represented by A, phthalic acid by P, and the diol component by HOXOH or X. Depending on the type, propane diol is shown by $X_p$, dipropylene glycol is shown by $X_{DP}$, and the symbol $X_{2E}$ is also used. Also, terminal alcohols are represented by the symbol O. The polymerization degree is an important factor in the composition, so it has been represented by a numerical suffix following ( ).

According to this invention, if phthalic anhydride is used as the dibasic acid, the reaction is started with one mole of this and one mole of a diol, and one mole of a monofunctional alcohol is added. In this esterification, an ester alcohol is obtained. A complex ester not containing (PX)$_n$ of high molecular weight can then be manufactured using this ester alcohol, and performing an addition transesterification reaction under reduced pressure. In the transesterification reaction, a completely equimolar reaction is impossible, so it is preferred to perform a quantitative reaction using a large amount of diester as far as possible. In the transesterification reaction, RPXOH is written instead of the RAXOH of (1), meaning that phthalic acid is used instead of adipic acid.

Herein, if ROH produced by heating the reaction mixture is removed, the product is obtained (Japanese Patent No. 2517245), but as a retroreaction occurs at the same time, (PX)$_n$ with n=3 or higher is produced as a side product when phthalic acid is used, and the viscosity increases.

According to this invention, the transesterification reaction is carried out under reduced pressure, preferably less than 100 mm Hg, more preferably less than 30 mm Hg, still more preferably within the range 0.2–25 mm Hg, and most preferably within the range 0.5–2 mm Hg. The reaction temperature is a high temperature in the vicinity of the boiling point of RAR, i.e., 160–250° C., but preferably 180–220° C., and it is preferred to carry out the transesterification by adding the components a little at a time.

If the number of moles of the diester RAR used in this reaction is 2 or less, the polymerization degree of the product is 2 or more, so it is preferred to use 2 moles or more to obtain a low viscosity product, but if it is more than this, the amount of RAR used for recycling increases and efficiency falls. If it is less than 1.5 moles, the product has a high viscosity and the advantage of this invention is no longer obtained. Regarding the composition of the product obtained, the yield is subtracted from the stoichiometric amount, and assuming that the number of moles of RAR in this number of grams had no effect on the reaction, the number of reaction moles and reaction proportion are calculated, and the inverse is calculated as the polymerization degree n of $(PX)_n$. $(PX)_2$ does not necessarily mean PXPXP, and in this reaction, it is thought to exert no influence on the reaction of ROH. The unit of the product has the structure PXAXP, which is thought to be the reason why a low viscosity product is obtained.

With adipic acid, unlike the reaction of the anhydride of phthalic acid, a selective reaction cannot be performed, but if the reaction between the diol and acid is given priority and a terminal alcohol is added, side production of the diester RAR is reduced. However, unless it is desired to selectively manufacture a bis compound of a complex ester with low n, it is better to use the components without modification which presents no problem for calculation of the polymerization degree. The number of moles of R(AX)nOH, R(PX)nOH may be computed and their proportions in the reaction calculated, assuming that the reaction product is a volatile component under reduced pressure, by removing the toluene used as an azeotropic material, unreacted terminal alcohol and 1-octanol, dividing the difference between the weight of the product and the calculated amount by the molecular weight of octanol to calculate the number of moles, and subtracting this from the usage amount. The inverse of this proportion is calculated as the polymerization degree n of $(AX)_n$. Although there may be differences in the reaction, the value is approximately 1.1–1.3, and it may be used to calculate the average molecular weight after removing ROH, but it may also be used without removing ROH and taking n=1 for the mixture.

With adipic esters, a retroreaction can partially be performed so that a composition having a wide molecular weight distribution is obtained, but by carrying out an addition transesterification under reduced pressure, higher molecular weights can be obtained. In this way, a polyester having the target polymerization degree can be manufactured as a low alcohol terminal product with a low acid value. Regarding the molecular weight distribution, a transesterification reaction takes place in the terminal part, but a transesterification reaction also occurs in the inner part of the polyester, and in the second position from the end, the retroreaction represented by equation (4) also takes place. Consequently, it is unlikely that a perfectly normal distribution would be obtained, but as the retroreaction due to ROH is controlled, the product probably has a molecular weight distribution close to a normal distribution.

In Example 16 described later, a polyester reaction was carried out to obtain a molecular weight of 3500 from a complex ester having a polymerization degree of 4, which was obtained directly from a sequential addition dehydration esterification reaction. It was noted that there was no side production of the low molecular weight diester RAR, therefore there was no need to remove a low molecular weight part by high temperature distillation after polymerization had taken place. On the other hand, in the reaction with the diol (Example 5), about 20 percent of RAR remained unreacted although twice the number of moles of R(AX)OH, the ester alcohol, was used, so it was calculated that the molecular weight increased to about 20% higher than that of the target composition.

It is well known that, among complex esters, water resistance improves by using a hetero complex ester. This objective can be achieved by manufacturing $R(AX)_nOH$ and $R(PX)_nOH$ separately or in admixture, determining the respective addition amounts depending on the target composition, adding different components before or after, and performing a transesterification reaction. A further feature of this invention is that the molecular weight and composition can be easily controlled depending on the purpose, and in particular, a substance can be provided wherein the acid value and alcohol value are effectively zero, and the alcohol terminal polyester with a limited molecular weight distribution can be provided.

The ester structure manufactured as the object of this invention is the reaction product represented by the following reaction equation and general formula (A):

$$R+n(A+X)+A+R \rightarrow R(AX)_nAR \qquad (A)$$

Herein, R (i.e., ROH) is a monofunctional alcohol or 4 or more carbon atoms having a straight chain or side chain, and in the examples, 2-ethylhexanol was used as it is generally used in the prior art. The alcohol is not limited to an alkyl alcohol. In ether alcohols referred to as ethylene glycol monoalkyl ethers, alcohols having different alkyl groups are used for antiseptic purposes, and ether glycols based on diethylene glycol may also be used. The dibasic acid represented by A (i.e., HOCOACOOH) is not limited to adipic acid or phthalic acid, but may also be an unsaturated acid such as succinic acid, glutaric acid, suberic acid, or partially, terephthalic acid, its hydrogen addition product or maleic anhydride. Two or more of these may be used in admixture. The diol represented by X (i.e., HOXOH) is selected from the viewpoint of low temperature properties required of a plasticizer and cost. Straight chain diols having 2–6 carbon atoms, or diols having a side chain such as 1,2 or 1,3-butane diol, 2-ethyl, 1,3-hexane diol, are used depending on the particular properties it is desired to stress, and ether alcohols such as di(poly)ethylene glycol, dipropylene glycol, can be used according to the purpose including hydrophilic affinity.

In the polyester structure of the prior art, in particular, composition was a problem and it was difficult to lower the acid value corresponding to the polymerization degree, hence in high molecular weight esters, the effect of transesterification was small, lower ester alcohols remained, and a polyester having an undesirable distribution was obtained.

In these terminal alcohol polyesters, the length of the chain structure corresponds to the molecular weight. When rigidity is required, short straight chain units are used, and when flexibility and water resistance are required, a chain diol having a side chain or a mixture of these units are used. They can be used as materials for higher polymer polyesters, and are useful as plasticizers corresponding to their viscosity and polarity. Polyethylene adipates of biterminal alcohols show excellent properties as plasticizers for polyethylene terephthalate (PET), and by making use of transesterification reactions, they can be used as polymerizable materials for biodegradable plastics. Complex esters are slightly different in the terminal alcohol, but their molecular weight is at least about 500 for n=1, and it is known that when they are used as plasticizers for polyvinyl chloride, they do not evaporate at all even if used continuously at 80° C. for 1 month. The removal of dibasic acid diesters which are also present as side products was a problem, and it was questionable whether or not this side production could be reduced to a negligible level. As they cannot be produced quantitatively, re-use of the side product diesters is required.

Use of Excess Alcohol in Esterification Reaction

If an excess of alcohol relative to acid is not used, as can be seen also from the equilibrium theory of the chemical reaction, it is not possible to make all the acid react without fail, however in these reactions, the excess amount must be reduced to the absolute minimum. Therefore, according to this invention, the reaction product is obtained by performing a reaction which partially goes through an ester alcohol.

In the aforesaid reaction equation (A), in the process R+A+X+A+R→RAXAR, the reaction takes place between reaction amounts of 2R and 2A, but if the reaction is partly designed so that {R+A+X}+{R+A+R}→RAX+RAR, more R can be used in a reaction between reaction amounts of 3R, 2A and X. If this reaction is performed, the preceding reaction also takes place at the same time, so there is no guarantee that all the product will be RAX even if an excess of R is used. In general, the reaction proceeds more rapidly with a monofunctional alcohol than with a diol and the majority of the product will be RAX+RAR, but due to the transesterification of the last step, RAX loses R, and the reaction is

RAX+RAR→RAXAR+R. This reaction cannot be carried out quantitatively, the sequential reaction RAX+RAXAR→RAXAXAR proceeds as a dependent reaction, unreacted RAR remains and the value of n in $R(AX)_nAR$ increases. Therefore, a product closer to the target substance is obtained the higher the molecular weight is, but with a lower complex ester, sequential reactions cannot be prevented. This means that pure RAXAR cannot be manufactured, but it is possible to design the reaction conditions so that the excess amount used is the absolute minimum. Next, when it is desired to make n=1, the value of n increases, so an excess amount of X is used in order to make the value of n large beforehand. If 2X is used, the reaction takes place with RAX+RAX+RA which is a reaction between 3R+3A+2X, and compared to when n=1 (1.5 moles of RAXAR), i.e., 3R+3A+1.5X, 0.5X more alcohol is used. n=1 cannot be produced, but by designing the reaction so that a higher value of n is obtained, an excess of alcohol can be used. Hence, the reaction takes place without a drop in reaction rate, and by selecting the reaction conditions, a drop in catalytic activity and a drop of reaction rate due to insufficient alcohol are prevented, and a product close to the target product can be manufactured.

Manufacture of Polyester

As a means of controlling molecular weight, it is important to control the reaction between the diol and dibasic acid unit. Depending on the diol component, it boils off together with water in the dehydration esterification reaction. Therefore, it is necessary to adjust the composition in the middle of the process. Further, it is possible that the composition will vary if the reaction is carried out in one step. The required amount of monofunctional alcohol to perform molecular weight control is used, but to obtain a homogeneous product, it is preferred to perform the polyesterification by adding half of the acid in small amounts prior to the reaction, and then adding the remaining half. In the case of an addition reaction between equivalents, the acid value does not fall sufficiently. Thus, the activated catalyst and excess amount of diol are added together when 90–95% of the reaction has taken place, and the reaction is then continued. Using the activated catalyst, the logarithm of the unreacted amount of acid calculated from the acid value is first order with respect to time, so the reaction endpoint can be predicted. On the other hand, as regards catalytic activity, the diol component may block the active sites which renders the catalyst inactive. Therefore, it may be necessary to add the activated catalyst while verifying the remaining amount of diol. The inactivation varies depending on the diol component. With ethylene glycol, the inactivation time is longest, and the concentration ratio with water during activation also has an effect. After reducing the acid value sufficiently using an activated catalyst, a transesterification reaction is performed between the ester alcohol produced by the excess diol used as an activation agent and polyester. A distillation apparatus is installed in the reactor, volatile components are removed under reduced pressure, the temperature is raised to 180–200° C., the degree of pressure reduction is increased to about 0.3 mm Hg, and the octanol produced (terminal alcohol component) is removed. Molecular weights are calculated beforehand including the diol component which is added together with the catalyst, and the reaction takes place in the compositional proportions of the three components. The corresponding terminal alcohol is then added, and an addition reaction performed. It is advantageous if the diol amount added last, is added together with the catalyst, and the effect of a small amount is larger the higher the molecular weight of polyester is. Even if only a very small amount of diol is used, the average molecular weight prior to transesterification may reach twice that subsequent to transesterification. The transesterification reaction takes place at the same time, and the excess of diol component used in the dehydration esterification reaction is probably in the form of an ester alcohol. The corresponding terminal alcohol is recovered in the transesterification reaction of the next step, and the ester polymerizes.

If the reaction molar amount is 2n moles and the excess diol is $X_E$, using one mole which is equivalent to (½n), the intermediate products and product are given by the following equation.

$2(n+1)A+2nX \rightarrow 2nAX+2A \rightarrow$ addition polymerization esterification of R → full esterification intermediate step $\{2R(AX)_nAR\}$ Next, addition of $X_E$ and catalyst → $R(AX)_nAX_E$+R 
$(AX)_nAR \rightarrow$ transesterification reaction →
$R(AX)_nAX_E(AX)_nAR$.

The molecular weight after transesterification increases correspondingly with the molar ratio of the number of moles of esterification reaction product and the number of moles of excess diol used, and a target product whereof the average polymerization degree varies according to its precision, is obtained.

Manufacture of Dibasic Acid Complex Ester

Describing now the manufacture of a complex ester of a dibasic acid such as adipic acid, it is very difficult to selectively perform a reaction between an acid and a diol, but it is most important to manufacture the ester so that no free acid remains. As it is effectively impossible to manufacture only a complex ester having n=1, the reaction is performed under the aforesaid conditions. Equimolar amounts of the dibasic acid and diol are reacted together under as mild conditions as possible. Fortunately, dibasic acids such as adipic acid have a high acid strength, and the dehydration esterification can be performed simply by heating. Herein, it is attempted to perform the reaction in a toluene solvent at 140–150° C. Finally, the temperature is raised to 160° C., and an equimolar reaction is performed. Simultaneously however, half of the terminal alcohol is gradually added, when the majority of the acid is allowed to react except a terminal acid, the remaining alcohol is then added and reacted. When 90–95% of the acid has been reacted, approximately 2.5 millimoles of an alkoxytitanium per 1 mole of acid is introduced into the diol component, a mixture of 1 g ethylene glycol and 0.5–1 g water is added, the activated catalyst is added, and the reaction is continued. It has already been stated that inactivation of the activated catalyst was found when using the diol component instead of ethylene glycol, but the extent of the effect differs depending on the type. If the reaction takes place smoothly, the reaction rate will differ depending on the reaction temperature, but the half-life of the acid can be arranged to be about 15–30 minutes, and the time at which the final acid value is obtained can be estimated. When the excess alcohol amount is small, the reaction is of course slower, so an excess diol catalyst liquid prepared in the same way may be added in portions as the reaction proceeds.

In this reaction, it may be expected that the acid diol reaction product reacts with acid to give AXA, but if an AXAX reaction takes place at the same time, some A will remain in excess. Strictly speaking, the latter reaction cannot be prevented 100%, but the target can be achieved by performing the reaction under mild conditions, and adding the monofunctional alcohol R in small amounts at a time. Excess diol may also react with the remaining A, but it probably first reacts with the product, forming an ester alcohol, and twice the number of moles of the monofunctional alcohol as the excess amount of diol are then produced in a transesterification reaction.

Regarding the effect of the excess used, the case will be considered where it is used in the final stage of the reaction due to differences of reaction type. Assuming that, in a reaction between 2 moles of terminal alcohol (R), 2 moles of dibasic acid (A) and 1 mole of diol (X), 0.1 mole of $X_E$, which is an excess of 10%, reacts:

A+X→AX→partial addition reaction of R {RAX+A, RA}→RAXA+R+0.1$X_E$
esterification→0.9RAXA+0.1RAX+
0.1RAX$_E$→transesterification reaction→
0.7RAXAR+0.2RAXAXAR (i.e., R(AX)$_{1.22}$AR)

If 10% of the acid is RAR produced as a side product, n is 1.22×1.25=1.53. Therefore, there is a problem in the reaction of the excess amount. Specifically, if the object is (RAXAR+RAXAXAR) or RAXAXAR, and an excess of X is used relative to A, the reaction proceeds with a correspondingly lesser amount of R. By using the lesser amount of R as the excess amount, the reaction may be made to proceed at the rate of the corresponding first-order reaction.

Manufacture of Hetero Complex Ester

When phthalic acid is used in the complex ester instead of adipic acid, a phthalate-phthalate (—PXPX—) structure is produced, and it is known that the viscosity of the product increases sharply. According to this invention, a method is proposed of quantitatively reacting the corresponding components. By using an activated catalyst, when the alcohol is insufficient, the reaction rate become slower, and it may be verified whether the reaction is proceeding quantitatively by verifying the rate. To carry out the reaction quantitatively, an esterification method is adopted wherein an excess is obtained by going through an ester alcohol as an intermediate. An identical method is adopted for phthalic acid, but the aforesaid phthalate-phthalate structure could not be eliminated. However, if a phthalate-adipate structure is adopted, use may be made of the smaller rise in viscosity. If the target reaction is (RPXAR+RPXAR+RPXAXAR+RPXAXPRR), there are 6 moles of X (diol) and 8 moles of R (terminal alcohol) for 5 moles of P (phthalic acid) and 5 moles of A (adipic acid), and for 1 mole of A, X is 1.2 and R is 1.6. In (5RPXAR), there are 1 mole of X and 2 moles of R for 1 mole of A. However, the reaction starts with 0.2 more X and 0.4 less R, and if additions are made so that finally, R is 2, an alcohol amount of 0.4 will be in excess. Esterification is performed, and after all the acid has been converted to ester, transesterification is performed. Thereby, 0.4 R corresponding to the excess is removed, and the product is obtained.

If the whole composition had the structure (RPXAR+RPXAR+RPXAXAR+RPXAXPR), RAR and RPR would not be produced as side products. However, as the reaction rate of phthalic acid is slow and adipic acid reacts first at low temperature, a mixture is produced containing mainly RPR as a side product. According to this method, as described above, adipate-phthalate is the main product, so its viscosity is relatively low at about 500 centipoise. From the viewpoint of the complex ester plasticizer test results of the prior art, expressing the plasticizer efficiency when used as a plasticizer for polyvinyl chloride in terms of the plasticizer amount which has an identical hardness to that of 50 parts of dioctyl phthalate, DOP, this value is estimated as 51–52. The target structure (RPXAR+RPXAR+RPXAXAR+RPXAXPR) is not limited to this combination.

If the structure has a high polymerization degree as in RPXAXAXPR, the RPR produced as a side product decreases, but if a large amount of phthalic acid is present, the viscosity rises. If the polymerization degree increases further, the viscosity increases and plasticizer efficiency is impaired.

Due to the use of this improved catalyst, a three component, and in the case of a hetero complex ester, four component quantitative reaction was observed. If any catalyst is used, this feature is not evident, and the fact that a quantitative reaction can be performed is important. Hence polyesters, complex esters and hetero complex esters which not only have a low alcohol termination with a low acid value, but also a narrow molecular weight distribution, can be manufactured. In the Examples, it is noted that the lower the molecular weight of the diol, the more volatile it is and the more easily it boils off together with water, which makes control difficult. These results are recorded in the Examples, but it should be understood that the invention is not limited by the type of diol component.

Hereafter, this invention will be described by means of specific examples, but it is not to be construed as being limited in any way thereby.

EXAMPLE 1

(Dehydration Esterification Reaction of Adipic Acid or Phthalic Acid)

0.65 g (36 millimoles) of water is added to and mixed with 1.49 g (24 millimoles) ethylene glycol, and 0.41 g (1.2 millimoles) tetrabutoxytitanium is added in small amounts at a time to give a gel-like mixture containing water.

10 g octanol is added to this gel-like polyolpolytitanic acid catalyst, stirred in and dispersed. The polyol-water activated titanium catalyst is then reacted at 200–205° C. using 1.2 millimoles to one mol of adipic acid. The acid value of the reaction liquid was measured. The time-related change of the acid molar amount computed from the acid value is shown in FIG. 1. This reaction is a first-order reaction of an acid, and was the same as in the case of the polyol polytitanate polytitanic acid of the above-mentioned patent, but its activity was remarkably improved, the rate did not change until the last stage, the acid concentration decreased, and the half-life was 11 minutes.

Likewise, the above-mentioned polyol-water activated titanium catalyst was reacted at 190–195° C. using 1.5 millimoles to 0.5 mols of phthalic acid. The acid value of the reaction liquid was measured. The time-related change of the acid molar amount computed from the acid value is shown in FIG. 1. The reaction was a first-order reaction, and the half-life was 13 minutes.

EXAMPLE 2

200 g of diester with an acid value of 0.6 was used for a transesterification reaction, which contains mainly dioctyl adipate, a small amount of dioctyl phthalate removed as pre-distillate on producing a complex ester, and acid produced by thermal decomposition. To this, 30 g of octanol was prevoiously added, followed by 1.2 millimoles of an ethylene glycol-water activated titanium catalyst for the transesterification reaction, and the mixture was heated with stirring at 200° C. for 1 hour. After 30 minutes, the acid value fell to 0.2, and after 1 hour, the acid value was 0.1 or less, i.e., effectively zero. The pressure was reduced, octanol was removed and the transesterification reaction was started.

EXAMPLE 3

Manufacture of Complex Ester-Polyester (Reaction Molar Ratio of Diol Diester and Diester=2:3)

0.5 moles (73 g) of adipic acid and one mole (134 g) of dipropylene glycol were placed in a dehydration esterification reactor, and an azeotropic dehydration esterification reaction was performed with a small amount of toluene. After 1 hour, 1.8 millimoles of the ethylene glycol-water activated titanium catalyst of Example 1 was added, the reaction was continued, and one hour after the addition, the acid value was 0.14. After a further 30 minutes, the reaction was terminated, toluene was removed, the reaction mixture was transferred to another reactor, and a transesterification performed. Specifically, 0.75 moles (277.5 g) dioctyl adipate (DOA) prepared beforehand was placed under a reduced pressure of 25 mm Hg at the water pump, a diol diester was added, and after 1 hour, an effectively stoichiometric amount of octanol was recovered.

4 ml of cooling water was added to the reaction liquid, stirred, a solvent was added, and the reaction mixture allowed to stand. Activated clay was then added, the filtrate was concentrated and distilled, and 56 g DOA with 282.4 g of distillation liquid residue were thereby obtained. The proportion of the number of moles obtained by subtracting the number of moles of DOA from the stoichiometric number of moles, by assuming the difference from the computational amount of 336.5 as the number of moles of DOA, was calculated. Taking the inverse of this and assuming that the polymerization degree has increased, the polymerization degree was 9.6, and the molecular weight of the polyester produced was 2712.

EXAMPLE 4

(Reaction Between Diol Diester and Diester in Reaction Molar Ratio of 1:2)

0.6 moles (80.8 g) of dipropylene glycol was introduced into 0.2 moles (29.2 g) of adipic acid and 0.1 moles (14.8 g) of phthalic anhydride, and a dehydration esterification reaction was started with a small amount of toluene. After 1 hour, 1.2 millimole of an active titanium catalyst was added. Three hours after the addition, the acid value (ml/g) was 0.11, and after a further 30 minutes, the reaction was complete. In another reactor, 1.5 moles of octanol was added to 0.6-moles adipic acid, and a dehydration esterification was started. After 30 minutes, 1.1 millimoles of an active titanium catalyst was added, and the reaction was carried out at 180–200° C. After 1.5 hours, the acid value was 0.03 ml/g. Octanol was removed under reduced pressure, and the aforesaid diol diester reaction liquid was added under reduced pressure at the water pump at 200° C. The octanol produced after 1.5 hours under 0.5 mm Hg at the vacuum pump was 79 g, corresponding to the approximate calculation amount.

After cooling, 4 ml of water was added, the reaction was stirred at 80° C. for 2 hours, activated clay filtration was performed, and the filtrate was concentrated and distilled under reduced pressure to give 52 g of a DOA fraction and 200.9 g of the product. Considering the difference from 259.4 g as DOA, the relative proportion of the number of moles from which this number of moles has been subtracted and the stoichiometric number of moles was calculated. From the inverse, the polymerization degree was 2.11 times, and the molecular composition was $O(AX_{DP})_{3.52}(PX_{DP})_{0.7}AO$, molecular weight 1414. It is determined that the complex ester of this composition has excellent water resistance and heating loss. In an example given in Japanese Patent Application Public Disclosure No. Hei 8-157418, results of experiments are shown for chemical amount: stoichiometry=1:2 The composition of the product is shown when desorption of phthalic acid removal (side product of DOP) due to the retroreaction and of diol components is suppressed to the minimum by the use of a diol diester. 2.11 times means that even if the reaction is performed for the purpose of n=1, the product has n=2.11. An extreme example of this is that a product of polymerization degree 2 containing 10% of polymerization degree 3 is possible. In practice, n=1 is ample, and as n progressively increases, the molecular weight distribution should become smaller.

EXAMPLE 5

(Hetero Complex Ester, Diol Diester:Diester=1:2.5)

608 g propylene glycol was added to 0.66 moles (98.7 g) of phthalic anhydride, and heated and stirred. After reacting the anhydride, 1.33 moles (194.7 g) of adipic acid were added, the mixture heated and stirred, and a reaction performed while removing the water produced. After about 1 hour, 1.8 millimoles of an ethylene glycol-water activated titanium catalyst was added. After 2 hours, the acid value was 0.07.

Propanediol was removed under reduced pressure, and 527.2 g diol diester was obtained as the remaining liquid.

For the formula:

$$76/(527.2/2-192.7)=1{,}072\,HO(X_pA)_{0.66*1.072}(X_pP)_{0.3*1.072}XOH$$

the molecular weight is calculated to be 282.5.

A dehydration esterification reaction was performed by heating and stirring 146 g of adipic acid and 300 g of 2-ethylhexanol, and removing the water produced. At 1.5 hours after starting the reaction, an octanol suspension of 1.5 millimoles of an ethylene glycol-water activated titanium catalyst was added, and after 1.5 hours, the acid value was 0.04 and the reaction was terminated. After distilling off and removing excess octanol from the reaction liquid, the pressure was reduced to 70 mm Hg, the reaction liquid was maintained at 210 or 180° C. under reduced pressure at the water pump, and 0.4 moles (113 g) of the aforesaid diol diester of molecular weight 282.5 was dripped into 1 mole of diester. Octanol was produced during the addition, removed by distillation, and when the approximate stoichiometric amount had been distilled off, the transesterification reaction was terminated. After cooling, 4 ml of water was added at about 100° C., the mixture was stirred and left overnight, and hydrolysis of the catalyst was terminated. Toluene dilution was performed, activated clay was added, and the mixture filtered. Next, the filtrate was concentrated, and distilled under reduced pressure at 0.5 mm Hg to obtain 160.2 g of dioctyl adipate as a side product. 218.8 g hetero complex ester was obtained as the liquid residue. The calculated value of the stoichiometric amount, 305 g−218.8=86/2, 86/2/370=0.233. The number of moles obtained from the reaction was 0.4−0.233=0.167.

The polymerization rate of the product is the inverse n=1/(0.167/0.4)=2.39. The molecular composition of the product was $O(AX_p)_{4.11}(PX_p)_{0.86}AO$, and the molecular weight was calculated to be 1312. In comparison with Example 24 of Japanese Patent Application Public Disclosure No. Hei 8-157418, it appears that in addition to water resistance, migration properties are sufficiently maintained.

EXAMPLE 6

(Reaction of Hetero Complex Ester, Molar Ratio=1:2.85)

A mixture of 1.79 moles (260 g) of adipic acid and 500 g octanol was placed in a dehydration esterification reactor, heated, and the water produced was removed. After 1 hour, 1.5 millimoles of an activated titanium catalyst was used, and 3 hours after the reaction was started, the acid value was 0.08. 40 g of the diester obtained in the above-mentioned Example 2 was added, and after adjusting to 1.9 moles of liquid, 0.666 moles (188 g) of the diol diester having a molecular weight of 282.5 obtained in Example 4 was added at 210–180° C./70–25 mmHg, and an octanol removal transesterification was performed. Post-treatment was performed as before. The catalyst was hydrolyzed, the mixture filtered, the solvent removed by distillation, and 349.8 g of product was obtained with 156 g of diester as a liquid residue. The same calculation as before was performed, giving n=2.685 and a product composition of $O(AX_p)_{4.61}(PX_p)_{0.96}AO$, molecular weight 1425. From this composition, propanediol was probably produced together with octanol in the transesterification reaction, but this could not be confirmed.

The distillation is performed at high temperature, and if a long time elapses, phthalic anhydride deposits in the distillation tube due to pyrolysis. Heat resistance extends to a maximum of 250° C., so in order to recycle DOA, the distillation must be performed below this temperature.

EXAMPLE 7

(Reaction Molar Ratio of Diol Diester and Diester=1:4)

A mixture of 4 moles (536 g) dipropylene glycol and 0.267 moles (39.5 g) phthalic anhydride was pyrolyzed, and the anhydride was reacted. 0.533 mols (78 g) adipic acid was added, heating dehydration was performed, and after 1 hour, a titanium catalyst was added to give an acid value of 0.08. Dipropylene glycol was removed under reduced pressure at 120° C., and 280.1 g of a liquid residue was obtained. A further 27 g of dipropylene glycol was added, and taken to have a molecular weight of 385. The aforesaid diol diester was added to 300 g DOA under reduced pressure, and a transesterification reaction was performed. The product of a 0.2 molar addition (molar ratio 1:4) was 162.5 g, and the side-product DOA which is recycled in this invention was 144.8 g. The product composition was $O(AX_{DP})_{1.94}(PX_{DP})_{0.39}AO$, and the molecular weight was calculated to be 946. The viscosity was 326 centipoises. The water resistance, measured by immersing a sheet in warm water at 60° C. and measuring the % loss, was 0.91 compared to a value of 0.8 for DOP. The loss on heating at 180° C. was 2.61 compared to 17% for DOP, and the softening temperature was −19.5° C.

EXAMPLE 8

(Diol Diester:Diester=3.37:1)

Following Example 7, 0.24 moles (92.3 g) was added to 300 g DOA, and a transesterification performed. The product yield was 182.0 g, and the amount of DOA which had to be recovered and recycled in this invention was 127.0 g. The composition was $O(AX_{DP})2.33(PX_{DP})0.47AO$, and the molecular weight was calculated to be 1062. Its viscosity was 334 centipoise, water resistance was 0.89, loss on heating at 180° C. for 2 hours was 2.03, and softening temperature was −19.0° C.

EXAMPLE 9

(Reaction Molar Ratio of Diol Diester and Diester=1:2.89)

Following Example 7, the reaction molar ratio was varied, 0.28 moles (92.3 g) diol diester was added to 300 g DOA, and a transesterification was performed. The product was 206.9 g, and the DOA to be recovered and recycled was 97.5 g. The product composition was $O(AX_{DP})_{2.52}(PX_{DP})_{0.551}AO$, and the molecular weight was calculated to be 1119. The viscosity was 393 centipoise. The plasticizing efficiency when used as a plasticizer was 51, approximately equivalent to that of dioctyl phthalate, DOP. The waterproofing test gave 0.69, heat loss at 160° C. was 2.65, which was much less, and the softening temperature was −16.5° C.

Examples 7–9 are examples given in Japanese Patent Application Public Disclosure No. Hei 8-157418 by the Inventor. Regarding the amount to be recycled required by this invention and the plasticity obtained, clear results are given, but the previous method of performing the composition calculation has been corrected to give the molecular weight. The plasticity of the complex ester disclosed in these Examples 7–9 is very good. This shows excellent antivolatility characteristics, but the generation of a large amount of DOA as a side product is a problem.

EXAMPLE 10

(Reaction of Ester Alcohol and Diester)

A dehydration esterification reaction was started using a mixture of 0.5 moles of adipic acid, 0.25 moles of 2-ethyl 1,3 hexane diol and 0.75 moles of octanol. After 1 hour, 1.7 millimoles of an activated titanium catalyst was added. 30 minutes later, the acid value was 1.66, one hour later it was 0.49, 1.5 hours later it was 0.05, and 30 minutes later the reaction was terminated. After the reaction was complete, the degree of pressure reduction in the reactor was gradually increased. Finally, the pressure was reduced by the water pump, the temperature was maintained at 200–210° C. for 1.5 hours, the pressure was maintained at 0.5 mm Hg for 30 minutes, and the octanol produced was removed. After the reaction was complete, water was added, the temperature increased, stirring performed for 3 hours, the mixture filtered to remove titanium residues, and evaporated under reduced pressure. 55.1 g of a DOA fraction and 102.7 g of the product were obtained. The composition was O(A $X_{2E})_{2.41}$AO, and the molecular weight was calculated to be 987. The performance when this was used as plasticizer is described for esters manufactured to obtain polymerization degrees of 1.5 and 2.5 in Japanese Patent Application Public Disclosure No. Hei 6-172261. In addition to plasticizer properties, due to the effect of the side chain at the 1,3 position of the diol component, the ester group is not easily attacked, and water resistance properties are excellent. As this excellent ester is a homopolymer, the viscosity and molecular weight distribution are close to those of a normal distribution, and it is also suitable for use as a plasticizer. In this reaction, alcohol is used in excess, so there is no problem when the acid value is lowered. When the catalyst is used to perform esterification in one step, various complex esters can be manufactured in a very short time provided that the molar ratio is maintained. Only removal and recycling of the diester which is used in excess is a problem. According to this invention, an amount which takes account of diester side production is used as the excess, and the DOA produced as a side product in the aforesaid reaction is added and recycled with a view to re-use in the transesterification.

EXAMPLE 11

A mixture of 1.2 moles (175.2 g) adipic acid, 0.6 moles (80.4 g) dipropylene glycol and 1.8 moles (234 g) octanol were placed under reduced pressure, the atmosphere replaced by nitrogen, and a dehydration esterification reaction started. After 1.5 hours at 180–200° C., when 90% of the water had been removed by distillation, an octanol suspension of 2 millimoles of an ethylene glycol-water activated titanium catalyst which had been prepared separately, was added. 1.5 hours after the addition, the acid value (ml/g) was 0.08, and after a further 30 minutes, the reaction was terminated. 0.6 moles (222 g) of dioctyl adipate, DOA, which had been prepared for recycling to the reaction liquid, was added, the temperature was lowered, the system was changed over to reduced pressure, and then the temperature was raised and held at 200° C. under a reduced pressure of 25 mm Hg at the water pump. During this process, octanol began to distil off, and after 1 hour, a diol diester solution, prepared separately, was added and the transesterification reaction continued. The diol diester solution was prepared by placing a mixture of 0.3 moles of phthalic anhydride and 0.6 moles (80.4 g) of dipropylene glycol in a nitrogen atmosphere, adding a small amount of toluene, and performing a dehydration esterification reaction at a temperature in the vicinity of 200–210° C. At the end of the reaction, 0.8 millimoles of an ethylene glycol-water activated titanium catalyst was added. 1.5 hours after the addition, the acid value was reduced to less than 0.1, and 30 minutes later, the product was used as an addition liquid. In the addition esterification reaction, if the addition is rapid, octanol distils off early, but the addition was made small amounts at a time while observing the amount of octanol released. The addition was complete after about one hour. Finally, the reduced pressure in the reactor was raised to 0.5 mm Hg, and all the octanol was removed together with part of the DOA. The octanol removed was approximately the stoichiometric amount, i.e., 152 g including the small amount of DOA. When the reaction liquid reached 100° C., 200 ml of toluene diluent and 6 ml of water were added, and the reaction mixture was left while stirring was continued. Next, activated clay filtration, concentration and reduced pressure concentration distillation were performed, fractions at 0.5 mm Hg up to a temperature of 250° C. were combined with the fraction from the previous transesterification, and 205 g of DOA were recovered. 465 g of the target complex ester, stoichiometric formula O(AX$_{DP}$)$_2$(PX$_{DP}$)$_{0.66}$AO, was obtained as a liquid residue, and the corresponding product was 408.4 g. The composition of the product was O (AX$_{DP}$)$_{3.03}$(PX$_{DP}$)$_{1.00}$AO, and the molecular weight was calculated to be 1373.

EXAMPLE 12

(Ester Alcohol-Diester Reaction/Molar Ratio RPXOH:R'AR'=1:2)

In Examples 12–18, the following symbols are used: A: adipic acid, P: phthalic acid, R: terminal alcohol (2 ethyl-hexanol), R': terminal alcohol (1-octanol), X$_{DP}$: dipropylene glycol used as diol component, X$_{13B}$: 1,3-butanediol used as diol component. The polymerization degree is indicated by ( ) with a subscript.

The diols and terminal alcohols are not limited to those in the Examples. The same reasoning can be applied to the diols and terminal alcohols (C$_4$–C$_{10}$ used and considered in the prior art.

The ethylene glycol-water activated titanium catalyst used in Examples 12–18 was prepared as follows. 0.65 g (36 millimoles) of water was added to ethylene glycol 1.49 g (24 millimoles) and mixed, 0.41 g (1.2 millimoles) of tetrabutoxytitanium was added in small amounts at a time, and a gel-like mixture containing water was formed. 10 g octanol was added to this gel-like polyol polytitanic acid, stirred and dispersed, and a polyol-water activated titanium catalyst was thereby obtained.

A mixture of 0.33 moles (49.6 g) of phthalic anhydride and 0.33 moles (44.7 g) of dipropylene glycol was stirred, and an anhydride reaction performed. 1.5 millimoles of the ethylene glycol-water activated titanium catalyst was then suspended in 0.33 moles (43.3 g) of 2-ethylhexanol, added to the reaction liquid, and a dehydration esterification performed. 1.5 hours after the addition, the acid value was 0.1, the reaction was continued for 30 minutes, and terminated. The reaction liquid was divided into two parts, and 66.4 g of this reaction product (0.166 moles for each mole of reaction product, RPXOH) was then added to the reaction liquid containing 0.34 moles (125.5 g) of dioctyl adipate (R'AR') and 0.8 millimoles of titanium catalyst under a reduced pressure of 5–1 mm Hg.

Corresponding to the addition, octanol containing toluene was distilled off, and 29.7 g was recovered. The addition transesterification was terminated, and when the temperature had fallen to 100° C., 5 ml of water was added, and the mixture stirred. After 2 hours, toluene was added and filtered by using active clay, and activated clay filtration was performed. The filtrate was distilled to remove solvent, volatile constituents (corresponding to R'AR', etc.) were removed at 190–250° C./0.5 mm Hg, and 73.6 g of product was obtained as the liquid residue.

32.1 g, the difference from the theoretical value of 105.7 g, is calculated to be 0.087 moles (mw=370) of dioctyl adipate, the proportion of the number of moles reacted, 0.08, is 0.477, and the inverse, 2.05, is the polymerization rate. As a result, the product is $R(PX)_{2.05}AR'$, molecular weight 911.2. The viscosity at 20° C. was 868 centipoise.

EXAMPLE 13

(Reaction Molar Ratio RPXOH:R'AR'=1:2.5)

A small amount of octanol was added to 160.2 g dioctyl adipate recovered in the reaction of 65.7 g (0.167 moles) of RPXOH ester mixed liquid obtained in the first step of Example 2, and stirred with an active titanium catalyst at 200° C. for 1 hour to make the acid value 0.06. Octanol was removed under reduced pressure, and addition performed with stirring at 5–0.5 mmHg. A transesterification reaction was performed for 1 hour, and after 30 minutes, post-treatment was performed as before, distillation was performed at 190–250° C./0.5 mm Hg, dioctyl adipate was removed as the pre-distillate, and the product was obtained as the liquid residue. The weight was 78.5 g, reaction molar number was 0.0935, proportion was 0.559, inverse n was 1.79, and viscosity at 20° C. was 664 centipoise.

EXAMPLE 14

(RPXOH:R'AR'=1:2.75)

0.33 moles (49.0 g) of phthalic anhydride and 0.33 moles (44.2 g) of dipropylene glycol were heated and stirred, 43.3 g (0.333 moles) of 2-ethylhexanol in which 1.2 millimoles of an ethylene glycol-water activated titanium catalyst was suspended, was added, and a dehydration esterification reaction was performed. After 2.5 hours, the acid value was 0.08, and after a further 20 minutes, the reaction was terminated.

A mixture of 200 g recovered dioctyl adipate and 76 g fresh dioctyl adipate was placed under reduced pressure. After heating to remove sufficient volatile constituents, the dehydration esterification reaction product was added over 1.5 hours at 190° C./0.5 mmHg with stirring, 42 g of the octanol produced was removed and the reaction was terminated. Water was added at 100° C., the catalyst was inactivated, and active clay filtration was performed. The filtrate was concentrated, distilled at 190–250° C./0.5 mm Hg, and 197 g dioctyl adipate was removed as a volatile constituent to obtain 157.9 g as the remaining liquid. The reaction molar number was calculated taking the difference from the stoichiometric amount of 209.5 g as diester. The inverse of its proportion, 0.576, gave a polymerization degree of 1.736. From this, the composition of the product was $R(PX_{DP})_{1.74}AR'$, and its molecular weight was calculated to be 829. The viscosity at 20° C. was 464 centipoises, estimated as $RPXA(XP)_{0.74}R'$, and it is thought that the viscosity was lower as it did not contain $(PX)_2$. Looking at the product when the reaction molar ratio was varied in the sequence 2, 2.5, 2.75, the polymerization degree falls in the sequence 2.05, 1.79, 1.74, and the viscosity gradually decreases accordingly, but when the polymerization degree exceeds 2, the viscosity rises sharply. When the viscosity increases, the plasticizing efficiency when it is used as a plasticizer for polyvinyl chloride correspondingly worsens, so in order to obtain outstanding plasticity, the reaction molar ratio is 2.5–2.75.

It is well known that water resistance and weatherability improve, the larger the number of phthalic acid units.

EXAMPLE 15

2 millimoles of an ethylene glycol-water activated titanium catalyst was added to a mixture of 0.7 moles (102.2 g) adipic acid, 0.7 moles (63 g) of 1,3 butanediol and 0.7 moles (91 g) of 1-octanol. After replacing air with nitrogen, the mixture was heated, and a dehydration esterification reaction was performed in the presence of a small amount of toluene. After 2 hours 15 minutes, the acid value was 0.10, and after a further 30 minutes, the esterification reaction was terminated. The product was concentrated under reduced pressure, toluene and 1-octanol were removed, and a yield of 214.2 g was obtained.

The amount, which is 16.8 g less than the calculation amount, was divided by 130 as octanol, and the analysis usage amount was corrected by 1.8 g, this gave a reaction molar amount of 0.585 moles, and a proportion of 0.837. The polymerization degree was 1.196, the composition was $R(AX_{13B})_{1.196}OH$ and the molecular weight was 369.3. 103 g, 0.278 moles of dioctyl adipate was heated, and maintained at 180° C./0.5 mm Hg with stirring, 0.58 moles, 214 g (0.58/0.278=2.08 times moles) of the aforesaid ester alcohol was added, and a transesterification was performed. The stoichiometric composition was $R(AX_{13B})_{2.08}AR'$, 74 g octanol was recovered from 0.278 moles, 218.6 g, and combined with the aforesaid amount to give the approximately quantitative amount. Post-treatment was performed as before, distillation was carried out under reduced pressure at 190–250° C./0.5 mm Hg to remove volatile constituents, and 195.6 g product was obtained as the residual product. The insufficient amount of 23 g was divided by the molecular weight of the diester, giving 0.062. The reaction molar number was 0.215, and its proportion was 0.776. The polymerization degree was the inverse, 1.28. The composition was $R(AX_{13B})_{2.68}AR'$, molecular weight 905.8. The viscosity at 20° C. was 224 centipoise.

EXAMPLE 16

2 millimoles of ethylene glycol-water activated titanium catalyst was added, together with a small amount of toluene, to 0.4 moles (58.4 g) adipic acid, 0.4 moles (36 g) of 1,3 butanediol and 0.4 moles (52 g) of 1-octanol, and a dehydration esterification reaction was performed. After 2.5 hours at 200° C., the acid value was 0.08. Toluene was removed under reduced pressure, and 130 g of the reaction liquid was used for the next reaction. A dehydration esterification was started with a mixture of 4 molar equivalents of adipic acid and 3 molar equivalents of 1,3-butanediol manufactured separately, and 2 molar equivalents of 1-octanol was added to perform the dehydration esterification to give to $R(AX_{13B})_{4.57}AR'$, molecular weight 1264. The viscosity at 20° C. was, 588 centipoise. 0.8 millimoles of tetrabutoxytitanium was added to 0.035 moles (44.2 g) of the latter compound, 130 g of the aforesaid ester alcohol was added in small amounts at a time over 1.5 hours at 180° C./0.5 mm Hg with stirring, a transesterification reaction was performed, and 50 g of the octanol produced was recovered. The filtrate from clay filtration for rendering the catalyst inactive was concentrated and distilled under reduced pressure by the standard method, volatile constituents were removed, and 122.0 g of product was obtained as the liquid residue. The volatile material did not contain fractions which boiled even at 250° C./0.5 mm Hg, so either the ester had reacted and disappeared, or it was not present. As 0.4/0.035=11.42 times the amount of RAXOH was made to react, the polymerization degree was 4.57+11.42=15.98, and the composition of the product was $R(AX_{13B})_{16}AR'$, molecular weight 3570. The viscosity at 20° C. was 1952 centipoise.

EXAMPLE 17

0.5 moles (58.5 g) of 2-ethylhexanol and 2.5 millimoles of an activated titanium catalyst were added together to a mixture of 0.3 moles (43.8 g) adipic acid and 0.15 moles (20.1 g) of dipropylene glycol, and a dehydration esterification reaction was performed. The product was a mixture of 0.15 moles each of RAXOH and R'AR'. $R(AX_{DP})_{1.2}OH$ and $R(PX_{DP})OH$ were also manufactured for a different purpose. 2 millimoles of the activated titanium catalyst was added to 0.5 moles of adipic acid, 0.5 moles of dipropylene glycol and 0.5 moles of 2-ethylhexanol, a small amount of toluene was added, a dehydration esterification reaction was performed at 200–210° C., and the acid value was lowered. Next, volatile octanol was removed under reduced pressure at 25 mm Hg, 100° C. or lower to obtain 176.2 g of product. The polymerization degree obtained by calculation was 1.20, the molecular weight was 422.8, and 0.3 moles thereof was used. $R(PX_{DP})OH$ was manufactured by the following method. 0.1 moles (13.4 g) of dipropylene glycol, 0.1 moles (13 g) of 2-ethylhexanol and 0.8 millimoles (0.3 g) of tetrabutoxytitanium were added to 0.1 moles (27.8 g) of dibutyl phthalate. The butanol produced by heating and stirring the reaction mixture at 180° C., first at ordinary pressure and then at 200 mm Hg, was removed. Approximately the stoichiometric amount, 14 g, of butanol was obtained, the reaction was terminated, and the product used for an addition reaction.

First, the solution of RAXOH+R'AR' was placed under reduced pressure, the temperature was raised with stirring, and the octanol produced was removed. The temperature was adjusted to 180° C., the reduced pressure was adjusted to 15 mm Hg, 0.3 moles (126.8 g) $R(AX_{DP})_{1.2}OH$ and 0.1 moles (39 g) $R(PX_{DP})OH$ were added, and a transesterification was performed. The octanol produced, approximately 70 g, was removed, and after 2 hours, the reduced pressure was raised to 0.5 mm Hg, the temperature was maintained for 30 minutes, and the reaction was terminated. Post-treatment was performed according to the standard method, the solvent was removed, distillation was performed under reduced pressure, and volatile constituents were removed to give 195.5 g of product as the residual substance. For a product stoichiometric value of $R(AX_{DP})_{3.4}(AX_{DP})_{0.66}AR'$, 206.3 g, n=1.24. The composition of the product was therefore $(AX_{DP})_{4.22}(PX_{DP})_{0.83}AR'$, molecular weight 1619. The viscosity at 20° C. was 820 centipoise.

EXAMPLE 18

Example Use of Propanediol
(RPXOH:R'AR'=1:2.7)

0.5 moles, 65 g of 2-ethylhexanol and 100 g of toluene were added to 0.5 moles, 74 g of phthalic anhydride, the mixture was stirred at 85–95° C. for 4 hours, and the anhydride was reacted. Next, 1 g tetrabutoxytitanium was introduced and dissolved in 56 g of 1,2-propanediol, i.e., 1.5 times the molar amount of 0.75 moles, an 0.8 g ethylene glycol-0.8 g water mixture was added with stirring, and the activated titanium catalyst was separated out to give a catalyst solution which was added to perform a dehydration esterification reaction. Water containing propanediol which had distilled off was returned to the reactor, the azeotropic solvent toluene was removed, the temperature was raised and the reaction was carried out to lower the acid value. After 4 hours, the remaining acid amount was 0.004 moles and the reaction was terminated. The remaining solvent and propanediol were removed under reduced pressure to give 164 g of 12-propanediol phthalate, $OcPX_pOH$. The difference from the stoichiometric amount of 168 g is due to the production of 12-propanediol phthalate, $HOX_pPX_pOH$, and the product contained a small amount of dioctyl phthalate. Its viscosity at 20° C. was 660 centipoise. 500 g (1.35 moles) of dioctyl phthalate (DOA) was added, the mixture was heated and stirred at 180–205° C., first under a slightly reduced pressure, next under the reduced pressure of the water pump and finally under 0.3 mm Hg, and 60 g of octanol which was a product of the transesterification reaction and had distilled off, was removed. The reaction mixture was cooled, a small amount of water and toluene were added at 100° C. and stirred, active clay was added to adsorb the titanium catalyst, and filtered to remove the catalyst. The solvent was distilled off from the toluene diluted solution, and finally, under 0.3 mm Hg, the temperature was raised to 260° C., 310 g of volatile constituents (DOA) was removed, and 234.4 g of product was obtained. The difference from the stoichiometric amount, 288 g, was 53.6 g DOA/370=0.145 moles, and the molar amount of the product was 0.355. Therefore, from (206n+370)×0.355=234.4, or from the inverse of the reaction amount per mole, the polymerization degree n=1.41. The composition was $O(PX_p)_{1.41}AO$, Mw=661. The viscosity of the product at 20° C. was 510 centipoise. In a comparison with viscosity, regarding plasticizer properties when used as a plasticizer for polyphenol chloride, the usage amount showing an equivalent value to when 50 PHR of DOP was used, was estimated to be 51–52. This is the same or slightly worse, but evaporation losses were almost negligible, and there was no worsening of low-temperature properties. Hence, it is considered that the product can be used as a plasticizer with excellent non-volatile properties. In this experiment, with esterification products for which the acid value does not decrease, the transesterification reaction does not proceed properly. Moreover, when volatile constituents are removed, phthalic acid anhydride, which is a pyrolysis product, separates in the distillation apparatus, and a water rinse-alkali rinse is required to lower the acid value. In this method, the production of phthalic acid diesters is reduced to the absolute minimum, and there are no side products due to the recycling of adipic acid esters. Therefore, a product of different polymerization degree m is produced depending on the reaction proportion with adipic acid diesters, a sharp rise in viscosity due to phthalic acid is prevented, and excellent plasticizer properties are obtained. Fractions in the polymerization degree indicate compositions having a higher degree. According to this method, phthalate-phthalate is not produced and phthalate-adipate is mainly obtained, so the viscosity of the product does not increase, and an excellent product is obtained.

EXAMPLE 19

(Object: di-2-ethylhexylpoly(15)ethane diol adipate (n=15, Molecular Weight 3000)

A mixture of 5 moles or 730 g of adipic acid, and 300 g of ethylene glycol, comprising 5×10/11 moles of ethylene glycol corresponding to a molecular weight of 2000, i.e., 281.8 g, and 18.2 g as a correction amount corresponding to diol which distils off azeotropically with water, were placed in a reaction vessel together with 100 g of toluene, the atmosphere was replaced by nitrogen, and a dehydration esterification reaction was started. The reaction was carried out while recycling and returning water which had azeotropically distilled off at 130–150° C. to the reaction vessel, and the water produced was removed. 5×2/11 moles or 118.2 g of 2-ethylhexanol, a terminal alcohol, corresponding to a molecular weight of 2000, was divided into three parts. Half was added from the beginning in small amounts at a time. After the water distilled off had exceeded half the amount, 100 g, the temperature was gradually raised, 22.5 g was added, and when it had exceeded 90%, the remaining 2-ethylhexanol, 379 g, was finally added. The temperature was lowered, 5 g tetrabutoxytitanium was dissolved in the difference, 8.8 g, from the ethylene glycol amount, 5×15/16, 290.6 g, corresponding to a molecular weight of 3000, a mixture of 2 g ethylene glycol and 1.5 g water was added with stirring, and the activated titanium was separated out. This activated catalyst suspension was added, and a dehydration esterification performed. While maintaining the reaction temperature at 200° C., esterification was carried out. The rate of the first-order reaction calculated from the logarithm of the remaining acid amount deduced from the final acid value and the time, gave a half-life of approximately 20 minutes. The remaining acid amount was 0.002, and after 30 minutes, the reaction was terminated.

Next, a distillation tube was attached, the reduced pressure was increased to 0.3 mm Hg, and the octanol which distilled off was removed. The transesterification reaction liquid was cooled, toluene and 1 g of water were added, and stirred. 40 g of activated clay was added, the mixture allowed to stand, the catalyst sedimented by adsorption, and filtered off from the supernatant liquid. Next, toluene was distilled off to give 920 g of a product [P]. The polymerization degree n was calculated as $\{[P]- 370\times51/\{5\times172\cdot[P]\}$. As n=15 corresponds to a molecular weight of 2950, the product had n=15.5 and the molecular weight was 3036. Thus, a polyester having a number average molecular weight of 3140 as determined by GPC, a weight average molecular weight of 6020, and an excellent distribution with a dispersion of 1.917, could be manufactured to a target molecular weight of 3000.

This polyethylene adipate is a polyester having a low acid value and containing almost no terminal alcohol. It has excellent miscibility will polyethylene terephthalate resin, and in an extrusion test using a 10 inch kneading machine, up to 8% could be added and mixed in. It was found that at 10%, dissolution was incomplete, and the substance flowed back to collect in the feed part. With other plasticizers, even 2-ethylhexyl phthalate and other complex esters, no ester was found which could be introduced in more than 3 parts. In a block polyester with polyethylene terephthalate prepared from polyethylene adipate of molecular weight 3000, up to 45 parts can be introduced under the aforesaid conditions, and it was found that in admixture therewith, the 8 parts could be increased to 15 parts.

EXAMPLE 20

(Object: di-2-ethylhexylpoly(6)1,3-propane diol adipate (n=6, Molecular Weight 1486)

80 g toluene was added to a mixture of 3 moles, or 438 g, of adipic acid, and 3×4/5 moles, or 182 g, of 12-propanediol as an amount corresponding to a molecular weight of 1114 with 35 g excess as the azeotropic distillation fraction with water, the atmosphere was replaced by nitrogen, and a dehydration esterification reaction was started. 3×2/7 moles, or 111 g, of 2-ethylhexanol was added in small amounts at a time while removing water at 130–150° C., the water which distilled off together with the propanediol during this process was recycled and returned to the reaction liquid, and the reaction was carried out until half the stoichiometric amount of water, 60 g, had distilled off. Subsequently, the temperature was raised to 170° C., the reaction was continued, and finally, (2/5–2/7) molar equivalents, 40 g, of 2-ethylhexanol was added. After 95% or more of the esterification had taken place, the temperature was lowered. 4 g of tetrabutoxytitanium was dissolved in a propanediol amount different from the amount corresponding to a molecular weight of 1500, 76×3×(6/7–4/5), or 13 g. The activated catalyst, which was obtained by adding a mixture of 1 g ethylene glycol- 1 g water, was added, esterification was carried out at approximately 200° C., the acid value was lowered corresponding to the first-order reaction, and its half-life was approximately 25 minutes.

Next, the product was placed under reduced pressure, a transesterification reaction was carried out at 210° C./0.3 mm Hg, and octanol, a volatile constituent, was removed. After the temperature had fallen to 100° C., toluene and 1 g water were added with stirring. The resulting activated catalyst was added, the separated titanium sedimented by aggregation, and was filtered to remove the catalyst. The solvent was removed by distillation, giving 631.5 g of a product [P] as the liquid residue. The polymerization degree n was calculated as $\{[P]-3\times370\}/\{3\times186-[P]\}$. For the polyester obtained, n=6.51, average molecular weight was 1581, and the effective average molecular weight by GPC analysis was 1600. The distribution was excellent with a dispersion of 1.98. The viscosity at 20° C. was 1440 centipoise. The error in the target molecular weight was related to the correction amount of the azeotropic fraction of propanediol. The excess amount due to azeotropic distillation is an amount obtained by determining the correction amount experimentally, and it should be modified depending on the recycling amount and reaction temperature. In particular, with propanediol, the correction amount must be computed to suit the molecular weight.

Polyester plasticizers are used as plasticizers for polyvinyl chloride, and their low volatility is well known. However, compared to diester plasticizers, they are high-cost and high viscosity, their plasticizer efficiency is poor and a large amount must be used. Due to these disadvantages, their range of applications was limited. Plasticizer polyesters with a molecular weight of 2000–4000, having a resistance to migration, are manufactured and marketed for use in conjunction with approximately 1000 polyesters and other resins. The method of this invention is low-cost due to the use of highly activated catalysts, and polyesters with no low molecular weight fraction and excellent molecular weight control can be selectively manufactured by transesterification reactions. Further, by selecting the diol component, a polyester having excellent low-temperature properties and viscosity properties can be manufactured.

EXAMPLE 21

(2-ethylhexyl 1,2-propanediol adipate)

The reaction molar ratio from the composition was adipic acid 2, diol 1 and octanol 2, and the reaction was performed with a reaction composition of adipic acid 2, diol 1.25 and octanol 1.5 (RAXAR+2RAXAXAR). Considering (2RAX+ 3RAXAR) as the intermediate composition, the usage amount of R is +2R, an esterification reaction was performed with this additional amount, and the amount corresponding to 2R was removed in the transesterification reaction to obtain the target product. This example is shown below.

1 mole of 146 g adipic acid, 47.5 g of 12-propanediol and 7 g as an excess amount were introduced into a reactor, a dehydration esterification reaction was performed at 140–150° C., and esterification was carried out while returning the aqueous layer to the reactor to recover propanediol. 65 g of 2-ethylhexanol was added when the water distillation amount was approximately half of the stoichiometric amount, 20 ml, the temperature was raised to 180–200° C., and the remaining 38 g was then added to perform esterification. Finally, 38 g (total amount is equimolar amount relative to acid) of 2-ethylhexanol was added as an additional amount. Subsequently, the temperature was lowered, 1.5 g tetrabutoxytitanium was dissolved in 10 ml toluene, and a mixture of 0.8 g ethylene glycol-0.8 g water was added with stirring. The resulting activated titanium catalyst was added, an esterification reaction was performed, and a reaction was performed with an approximate half-life of 20 minutes.

Finally, with the system under reduced pressure at 200° C./0.3 mm Hg, a transesterification was performed to remove volatile constituents, and the reaction was terminated. Toluene-water was added, active clay was added, the catalyst was filtered and the solvent was removed by distillation. The temperature was raised to a maximum of 270° C. at a reduced pressure of 0.3 mm Hg to remove DOA by distillation, and 201.5 g of a product [P] was obtained as the liquid residue. The viscosity at 20° C. was 140 centipoise. The difference from the yield of 278 g calculated from one mole of adipic acid with n=1 was 76.5/370=0.206 as the number of moles of DOA. Further, using a value of 1−0.206=0.793 as the number of moles which reacted as complex ester, n is calculated to be {[P]−370×(1−0.206)}/{186×(1−0.206)−[P]}, so n=1.70. The excess of propanediol used is the amount that distils off as an azeotropic component together with water found by experience from preceding experiments. Theoretically, if the target composition is obtained, n=1.66, but it is extremely difficult to obtain a quantitative reaction excluding the azeotropic fraction, and this is the first time that a polymerization degree of 1.70 has been obtained directly by this method. If a complex ester having a small n or other diols are used, n=1.4 is obtained by the direct method. This reaction is insufficient if the alcohol amount does not react quantitatively, or intermediate products of ester alcohols remain, and the rate of the first-order reaction is remarkably slowed. Conversely, it can be determined from the reaction rate whether the reaction has proceeded quantitatively. From the viscosity of the product obtained, it was estimated that although plasticizer efficiency was 10% less when the ester was used as a plasticizer for polyvinyl chloride, it had excellent properties exhibiting an identical surface hardness. It had low-temperature properties, and is expected to be used as a plasticizer with very little volatility even when used for long periods.

EXAMPLE 22

Manufacture by Recycling Method Using Propanediol (2-ethylhexyl poly(1,7) 1,2 propanediol adipate)

The boiling point of 1,2 propanediol is low and it distils off azeotropically with water, so it is very difficult to perform the reaction quantitatively. An example will now be given where, assuming that dioctyl adipate, DOA (may be abbreviated as RAR) is produced as a side product, this side product DOA is used. This is an example where, in the same way as a reaction is performed with recovered DOA using an ester alcohol corresponding to RAX, a complex ester is manufactured by producing RAX while partly producing DOA simultaneously, and reacting this with recovered and recycled RAR.

1.5 moles, 219 g of adipic acid, 1 mole, 76 g of 1,2 propanediol, and 15 g excess amount as the azeotropically distilling fraction, were placed in a reactor, the atmosphere was replaced by nitrogen, and the reaction was started at 140–160° C. The reaction was carried out while recycling and returning water which distilled off to the reactor, and half the amount of octanol, 1 mole, 130 g, was simultaneously added in small amounts at a time. Propanediol was sufficiently reacted, and after approximately half the stoichiometric amount of water had been discharged, the temperature was raised to 180–200° C., and the reaction was continued while adding 90 g of octanol. Finally, the temperature was lowered, 3 g tetrabitoxytitanium was dissolved in 40 g octanol, and a mixture of 1 g ethylene glycol-1 g water was added with stirring. The resulting activated titanium suspension was added, and a dehydration esterification reaction was performed.

The excess amount of alcohol corresponds to the molar amount of diol, and the reaction was carried out with a half-life of approximately 20 minutes.

After the acid value was sufficiently lowered, the reaction mixture was placed in the recovered DOA, 740 g, placed under reduced pressure at a temperature of 180–200° C. with stirring, and the solvent and octanol produced by transesterification were removed.

Finally, the pressure was lowered to 0.3 mm Hg to sufficiently remove octanol, and the reaction was terminated. When the temperature had fallen to 100° C., 400 ml toluene and 2 ml water were added with stirring, 40 g of active clay was added with stirring, and the mixture allowed to stand to sediment the catalyst. Subsequently, the mixture was filtered, the solvent was distilled off, and finally DOA was removed under reduced pressure at a maximum temperature of 270° C./0.3 mm Hg. Its amount was 674 g. The product was 406 g as the liquid residue, the difference from the stoichiometric amount, 556 g, produced from one mole of reacted adipic acid, i.e., 150 g, was 405 moles of DOA, and the amount reacted with the complex ester of adipic acid was 2−0.405=1.595 moles. From the following equation:

(186n+370)×1.595/n+1=406, n=1.68. Therefore, the molecular weight was 682.

This is an example where RAX is produced and reacted while partly producing RAR, which is recycled and consumed. RAX can also be produced as the object, in which case a target product corresponding to RAXAR is partly produced simultaneously. In the transesterification reaction, the obtaining of a reaction liquid containing RAXAR is a difference, but if the excess of RAR does not undergo transesterification, a complex ester having a small value of n cannot be obtained. This is the same in this example, the value of n becoming smaller the larger the proportion of RAR in the reaction.

EXAMPLE 23 di-2-ethylhexyl poly(1,4) 1,2 propaneoxy 1,2-propanediol adipate (dipropylene glycol bis-2-ethylhexyl adipate)

2 moles, 292.2 g of adipic acid, and 1.1 moles (0.1 moles excess), 147 g, of dipropylene glycol were introduced into a dehydration esterification reaction apparatus, and the atmosphere was replaced by nitrogen. The reaction was performed at 140–160° C., and 130 g of 2-ethylhexanol was added in small amounts at a time up to 40 ml as water distilled off. The temperature was raised, the remaining 100 g was continuously added in small amounts at a time, and when more than 90% had been added, an activated titanium catalyst, produced by dissolving 3 g tetrabutoxytitanium in 30 g of 2-ethylhexanol and adding a mixture of 1 g ethylene glycol-1 g water with stirring, was added and the reaction was performed at 200° C. The half-life of the first-order reaction was 20 minutes.

After performing the transesterification reaction at 200° C., toluene and water were added, and hydrolyzed. Active clay was added, and the catalyst was separated by sedimentation filtration, and the filtrate was concentrated. Finally, the temperature was raised to a maximum of 260° C. at 0.3 mm Hg to remove volatile DOA, and 414 g of product was thereby obtained. The average polymerization degree of the product was calculated to be 2.17, and its viscosity was 460 centipoise. With diols of low volatility, a rapid reaction can be performed, but the fact that the reaction composition is inadequate deviates from the target.

EXAMPLE 24 di-2-ethylhexyl 1,2-propanediol adipate phthalate (Example of Manufacture of Hetero Complex Ester)

If the target compound is (2RPXAR+RPXAXAR+RPX-AXPR), with 5 moles of P, A, 6 moles of X and 8(5+3) moles of R, and considering (2RAX+3RPXAR+RPXPR) as an intermediate, an excess of 2 moles of R can be used. If the corresponding amount 2R is removed in a transesterification reaction, the target composition is obtained. An example of the reaction using 1 mole of phthalic acid on a molar scale of 1/5, is shown below.

130 g of 2-ethylhexyl alcohol and 80 g toluene as solvent were added to 148 g of phthalic anhydride, the atmosphere was replaced by nitrogen, and the reaction mixture was heated at 80–95° C. for four hours with stirring to react the anhydride. 146 g adipic acid, 91.2 g (1.2 times moles) of 1,2 propylene diol and 8.5 g as the amount distilling off azeotropically together with water, were added, and a dehydration esterification reaction was started. An esterification reaction was carried out a 140–150° C., water which distilled off was recycled four times and returned to the reactor, and on each occasion the temperature was lowered to distil off the water and remove it. During this time, 78 g 2-ethylhexanol was added in small amounts at a time, and after 36 ml water had been discharged, the temperature was raised to 190–210° C. for the the reaction. After 90% of the water had been discharged, 52 g octanol was added, and the temperature wad lowered. Separately, 3 g of tetrabutoxytitanium was dissolved in 10 g toluene and 15 g octanol, and a mixture of 1.5 g ethylene glycol-1.5 g water was added with stirring to produce an activated titanium catalyst. This was added to the reactor to continue the esterification, and after 3 hours, the reaction was terminated.

After cooling, 300 ml toluene was added and stirred together with 2 ml water, then active clay was added to sediment the catalyst by adsorbtion. The mixture was filtered, the filtrate was concentrated, and distilled under reduced pressure at 0.3 mm Hg. The temperature used was 210–220° C., and a dioctyl phthalate fraction having a boiling point of 210–220° C. was obtained. The difference of 168.8 g from the stoichiometric production amount of PRXAR, 576 g, was considered to be RPR. From a number of moles of 0.432, the molar amount which reacted as complex ester was 2−0.432=1.568. Calculating n={390× 1.568−407.2}/{186×1.568−407.2}, n=1.76 and the molecular weight was 717.7. The empirical formula was shown by $R(AXP)_{1.76}PR$, and the vescosity at 20° C. was 540 centipoise. When used as a plasticizer, it showed approxmately identical performance to that of phthalic acid diesters, and is expected to be a plasticizer without any volatility.

This hereto complex ester may be manufactured using PRX phthalic acid ester alcohol instead of RAX in the recycling method shown in Example 22.

The invention claimed is:

1. A catalyst for an esterification reaction or a transesterification reaction, which is a gellike substance comprising a mixture of an ailkoxytitanium, water-soluble polyol and water, or the reaction product thereof, wherein the number of moles of said water-soluble polyol and said water relative to 1 mole of titanium, is respectively 1–50 moles and 1–60 moles.

2. The catalyst according to claim 1, wherein said alkoxytitanium is tetrabutoxy titanium, tetraisopropyloxy titanium or tetraoctyloxytitanium, and said water-soluble polyol is ethylene glycoL propanediol, diethylene glycol or glycerine.

3. A method of producing an ester comprising, a first step wherein a monofunctional alcohol and diol are simultaneously or separately added to a dibasic acid, a second step wherein the reaction product of said acid and alcohol produced in the first step is separated to obtain an ester, and a third step wherein the reaction product separated, in the second step is recycled to the first step, 0.05–5 millimoles of the catalyst according to claim 1 or 2 relative to one mole of acid being used in said first step.

4. A method of producing an ester comprising, a first step wherein a diol is reacted with an ester produced beforehand from a dibasic acid and a monofunctional alcohol, or an ester produced beforehand from a monofunctional alcohol and diol, a second step wherein unreacted ester is separated from the product produced in the first step to obtain another ester, and a third step wherein unreacted ester separated in the second step is recycled to the first step, 0.05–5 millimoles of the catalyst according to claim 1 or 2 relative to one mole of acid being used in said first step.

5. A method of producing an ester comprising a step of reacting a reaction product, comprising an ester composition $(RO(COACOOX)_nH)$ ($n \geq 1$) formed from the reaction of a dibasic acid (HOOCACOOH), diol (HOXOH) and terminal alcohol (ROH), in the presence of a catalyst according to claim 1 or 2 under a reduced pressure of 100 mm Hg or less.

6. The method according to claim 5, wherein said reaction product further contains an ester compound represented by the general formula:

(in the formula, R' are alkyl groups, which may be identical or different and may be identical to R).

7. A method of producing an ester comprising a step of a dehydration esterification reaction and a following transesterification reaction of a dibasic acid, diol and monofunctional alcohol using the catalyst according to claim 1 or 2, wherein the required amounts of said monofunctional alcohol and said diol are distributed and continuously introduced, into a reactor over the whole period of the esterification reaction.

8. The method according to claim 7, wherein said dehydration esterification reaction is performed under conditions such that a complex ester and ester alcohol are produced and coexist together.

9. The method according to claim 7, wherein said ester is represented by $R(AX)_{m+n}AR$ ($m \geq 0$, $n \geq 1$, A is a dibasic acid, X is a diol and R is a monofunctional alcohol, the reactive groups and ester bonds being omitted), the amount of said monofunctional alcohol (R) used in said dehydration esterification reaction is obtained by adding 0.2–2.0 times the difference between the amount required to obtain $R(AX)_mAX+R(AX)_{n-1}AR$ as the product of the dehydration esterification reaction and the stoichiometric amount required to obtain $R(AX)_{m+n}AR$, to the stoichiometric amount required to obtain $R(AX)_{m+n}AR$.

10. The method according to claim 7 or 8, wherein the molecular weight distribution of the esters is 2 or less.

11. A method according to claim 3, wherein said alkoxytitanium is tetrabutoxy titanium, tetraisopropyloxy titanium or tetraoctyloxytitanium, and said water-soluble polyol is ethylene glycol, propanediol, diethylene glycol or glycerine.

12. A method according to claim 4, wherein said alkoxytitanium is tetrabutoxy titanium, tetraisopropyloxy titanium or tetraoctyloxytitanium, and said water-soluble polyol is ethylene glycol, propanediol, diethylene glycol or glycerine.

13. A method according to claim 5, wherein said alkoxytitanium is tetrabutoxy titanium, tetraisopropyloxy titanium or tetraoctyloxytitanium, and said water-soluble polyol is ethylene glycol, propanediol, diethylene glycol or glycerine.

14. A method according to claim 7, wherein said alkoxytitanium is tetrabutoxy titanium, tetraisopropyloxy titanium or tetraoctyloxytitanium, and said water-soluble poiyoi is ethylene glycol, propanediol, diethylene glycol or glycerine.

15. A method according to claim 14, wherein said dehydration esterification reaction is performed under conditions such that a complex ester and ester alcohol are produced and coexist together.

16. A method according to claim 15, wherein said ester is represented by $R(AX)_{m+n}AR$ wherein $m \geq 0$, $n \geq 1$, A is a dibasic acid, X is a diol and R is a monofunctional alcohol, the reactive groups and ester bonds being omitted, the amount of said monofunctional alcohol (R) used in said dehydration esterification reaction is obtained by adding 0.2–2.0 times the difference between the amount required to obtain $R(AX)_mAX+R(AX)_{n-1}AR$ as the product of the dehydration esterification reaction and the stoichiometric amount required to obtain $R(AX)_{m+n}AR$, to the stoichiometric amount required to obtain $R(AX)_{m+n}AR$.

17. A method according to claim 14, wherein the molecular weight distribution of the esters is 2 or less.

18. A method according to claim 15, wherein the molecular weight distribution of the esters is 2 or less.

* * * * *